US012606524B2

(12) United States Patent
Wilkinson et al.

(10) Patent No.: US 12,606,524 B2
(45) Date of Patent: Apr. 21, 2026

(54) SYNTHESIS OF PYRROLE ACID DERIVATIVES

(71) Applicant: INFEX Therapeutics Limited, Macclesfield (GB)

(72) Inventors: Andrew Wilkinson, Macclesfield (GB); Ian Cooper, Macclesfield (GB); David Orr, Macclesfield (GB); Jonathan Finlayson, Macclesfield (GB); Adam Bunt, Macclesfield (GB); James Kirkham, Macclesfield (GB); David Lyth, Macclesfield (GB); Kevin Blades, Macclesfield (GB)

(73) Assignee: INFEX Therapeutics Limited, Macclesfield (GB)

( * ) Notice: Subject to any disclaimer, the term of this patent is extended or adjusted under 35 U.S.C. 154(b) by 430 days.

(21) Appl. No.: 18/246,777

(22) PCT Filed: Oct. 6, 2021

(86) PCT No.: PCT/GB2021/052580
§ 371 (c)(1),
(2) Date: Mar. 27, 2023

(87) PCT Pub. No.: WO2022/074385
PCT Pub. Date: Apr. 14, 2022

(65) Prior Publication Data

US 2023/0286915 A1 Sep. 14, 2023

(30) Foreign Application Priority Data

Oct. 7, 2020 (GB) ..................................... 2015885

(51) Int. Cl.
*C07D 207/48* (2006.01)

(52) U.S. Cl.
CPC .................................. *C07D 207/48* (2013.01)

(58) Field of Classification Search
CPC .................................................... C07D 207/48
See application file for complete search history.

(56) References Cited

U.S. PATENT DOCUMENTS 11,459,296 B2 * 10/2022 Cooper ................ C07D 401/10
11,845,725 B2 * 12/2023 Cooper ................ C07D 207/36

FOREIGN PATENT DOCUMENTS

WO WO-2019/220125 A1 11/2019
WO WO-2021/099793 A1 5/2021

OTHER PUBLICATIONS

International Preliminary Report on Patentability for International Application No. PCT/GB2021/052580 dated Dec. 14, 2023.
Gao et al., "Synthesis of Pyrroles by Click Reaction: Silver-Catalyzed Cycloaddition of Terminal Alkynes with Isocyanides", Angewandte Chemie International Edition, vol. 52, No. 27, Apr. 29, 2013 (Apr. 29, 2013), pp. 6958-6961.
International Search Report and Written Opinion for Application No. PCT/GB2021/052580 dated Dec. 14, 2021.
Shan et al., "A Copper-Catalyzed Three-Component Reaction for the Preparation of Polysubstituted Pyrroles from Alkynyl Ketones, Amines and Isocyanoacetates", ChemistrySelect, vol. 4, No. 32, Aug. 28, 2019 (Aug. 28, 2019), pp. 9497-9500.
Great Britain Search Report for GB Application No. GB2015885.3 dated Mar. 31, 2021.

* cited by examiner

*Primary Examiner* — Golam M Shameem
(74) *Attorney, Agent, or Firm* — Foley Hoag LLP; Dana M. Gordon; Shejla S. Pollozi

(57) ABSTRACT

This invention relates to the synthesis of compounds that can be used to treat bacterial infections in combination with other antibacterial agents, and more specifically in combination with a class of antibacterial agents known as carbapenems. The compounds resulting from the novel methods of the present invention are enzyme inhibitors and more particularly are metallo-β-lactamase inhibitors.

3 Claims, No Drawings

SYNTHESIS OF PYRROLE ACID DERIVATIVES

RELATED APPLICATIONS

This application is a U.S. National Stage filing under 35 U.S.C. § 371 of PCT Application No. PCT/GB2021/052580, filed Oct. 6, 2021; which claims the benefit of priority to Great Britain Application No. 2015885.3, filed Oct. 7, 2020.

This invention relates to the synthesis of compounds that can be used to treat bacterial infections in combination with other antibacterial agents, and more specifically in combination with a class of antibacterial agents known as carbapenems. The compounds resulting from the novel methods of the present invention are enzyme inhibitors and more particularly are metallo-β-lactamase inhibitors.

Each year, throughout Europe, over 4 million people contract a healthcare associated bacterial infection, resulting in ~37,000 deaths (Public Health England). The increasing prevalence of multi-drug resistant bacteria has worsened patient outcomes, prolonged hospital stays and necessitated use of 'last resort' and potentially toxic antimicrobials, such as colistin and polymyxin B. It has been estimated that by 2050, without intervention, antibiotic-resistant bacteria will cause the death of over 10 million people each year, and this will equate to an economic burden of 100 trillion US dollars.

In the clinic, antibiotic-resistant Gram-negative pathogens cause diverse infections, including pneumonia, blood stream infections, surgical site infections, skin and soft tissue infections, and urinary tract infections. There are limited effective treatment options for these organisms and empirical antibiotic therapy often fails in patients infected with Gram-negative organisms of the ESKAPE pathogen group (*Enterococcus faecium, Staphylococcus aureus, Klebsiella pneumoniae, Acinetobacter baumannii, Pseudomonas aeruginosa*, and *Enterobacter* species).

In February 2017, the World Health Organisation (WHO) issued a prioritised list of bacterial pathogens to assist member states in focusing research and development to the areas of greatest need. Of these bacteria, the WHO classed the following Gram-negative organisms as a critical priority: carbapenem resistant *A. baumannii*; carbapenem resistant *P. aeruginosa*; carbapenem resistant and ESBL-producing Enterobacteriaceae (including *K. pneumoniae* and *E. coli*). Consequently, carbapenem-resistant Gram-negative bacteria have been defined as a critical unmet medical need. The mode of action of β-lactams, such as carbapenems, involves covalently binding to the active site of transpeptidases that link peptidoglycan chains of the bacterial cell wall. This results in inhibition of cell wall synthesis and ultimately cell death. The advantage of carbapenems is a broader spectrum of activity compared with most other β-lactams and until recently their use had not been significantly impacted by resistance development.

The use of carbapenems as a last line of defence against multi-drug resistant Gram-negatives has been compromised by the emergence of carbapenemases from the metallo-β-lactamase (MBL) class. These enzymes bind to carbapenems and cleave the β-lactam ring, resulting in antibiotic deactivation. The Ambler classification system divides known β-lactamase enzymes into four classes according to amino acid sequence. Classes A, C and D β-lactamases cleave β-lactams through transient binding of a serine group within the enzyme's active site to the carbonyl of the β-lactam ring. This results in formation of an acyl-enzyme and cleavage of the β-lactam ring. Subsequently, an activated water molecule deacylates the acyl-enzyme intermediate, hydrolysing the bond between serine and carbonyl, releasing the deactivated β-lactam. MBLs are mechanistically and structurally discrete from class A, C and D serine-β-lactamases. In this case, cleavage of β-lactams occurs in a single step, without formation of a covalent intermediate. MBLs coordinate water molecules and zinc ions to His, Cys and Asp residues in their active site, where water molecules facilitate nucleophilic attack and bond cleavage within the β-lactam ring. The subclasses of MBLs are structurally divergent, with B1 and B3 enzymes containing two zinc ions in the active site and displaying a broad substrate profile. Group B2 enzymes rely upon a single zinc ion and hydrolyse only carbapenems. Clinically, MBLs of the B1 class, including NDM, VIM and IMP, are most prevalent and are frequently identified within mobile genetic elements.

Pre-existing serine-β-lactamase inhibitors (effective against Ambler Class A, C and some Class D β-lactamases) have successfully restored activity of numerous β-lactams. Inhibitors bind to the active site of the enzyme transiently or permanently with high affinity, effectively outcompeting binding of β-lactams. Marketed β-lactam/β-lactamase inhibitor combinations include amoxicillin and clavulanic acid (Co-amoxiclav) and ceftazidime and avibactam (Avycaz). Currently, there are no metallo-β-lactamase inhibitors (MBLIs) in clinical development or clinically available, indicating commercial potential for a broad spectrum MBLI that restores the activity of carbapenems.

The first carbapenem used clinically was imipenem, for the treatment of complex microbial infections. A disadvantage of imipenem is its hydrolysis in the mammalian kidney by dehydropeptidase I (DHPI) necessitating co-formulation with the dehydropeptidase inhibitor cilastatin. Subsequent carbapenem iterations, including meropenem, are insusceptible to DHPI hydrolysis due to the presence of a methyl group at the 1-β position of the carbapenem moiety. Meropenem is less potent than imipenem against Gram-positive pathogens but has enhanced potency against Gram-negative organisms and is employed widely in the clinic. To combat resistance to carbapenems, we have discovered a series of compounds that inhibit metallo-β-lactamase enzymes. The compounds significantly improve the efficacy of meropenem against drug resistant bacteria when co-administered with meropenem. The invention relates specifically to methods of forming these compounds.

It is contemplated that other approved carbapenems might also benefit from co-formulation with the compounds of the invention. Other currently approved carbapenems include: ertapenem, doripenem, panipenem, biapenem and tebipenem.

Until comparatively recently, bacterial infections were one of the most common causes of death, disfigurement and disablement. During the $19^{th}$ century a series of antibiotic drug classes were developed, meaning that the successful treatment of bacterial infections has become routine. However, microbial resistance to antibiotics is becoming a significant problem and many consider that this will become one of the most significant challenges to human health. Indeed, in some bacterial pathogens, multidrug resistance has already become common.

The greatest unmet medical need is the dearth of effective treatments for multidrug resistant Gram-negative bacteria. Therefore discovery of novel antibiotics that are active against WHO listed pathogens of critical concern, or drugs that circumvent existing bacterial resistance mechanisms is essential.

WO2019/220125 and GB1916915.0 (unpublished) disclose a series of compounds which are inhibitors of metallo-β-lactamases used in combination with antibacterial agents to treat bacterial infections.

It is an aim of certain embodiments of this invention to provide alternative methods of synthesising metallo-β-lactamase inhibitors. It is an aim to provide methods of synthesising metallo-β-lactamase inhibitors which are more scalable, provide purer product or are more resource efficient than those previously disclosed.

BRIEF SUMMARY OF THE INVENTION

In each of the below aspects of the invention, the compounds of formulae (I) to (XIX) may be a free acid or free base as shown, or may be a pharmaceutically acceptable salt thereof.

In a first aspect of the invention is provide a method of forming a compound of formula (IV) or a pharmaceutically acceptable salt thereof, the method comprising:

(a) reacting the compound of formula (I) with the compound of formula (II) in the presence of Pd/C to form the compound of formula (III):

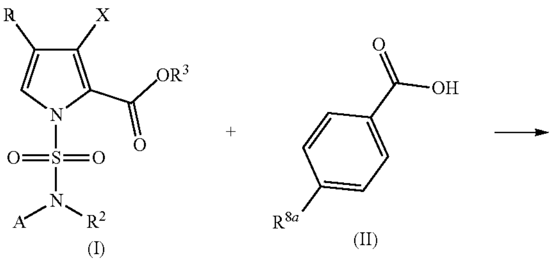

(I) (II)

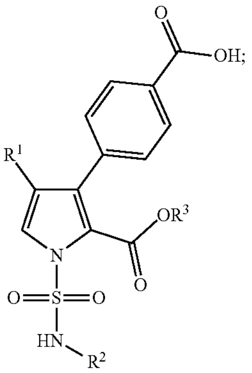

(III)

and (b) forming a compound of formula (IV) or a pharmaceutically acceptable salt thereof from the compound of formula (III):

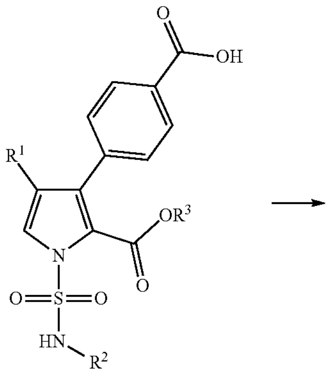

(III)

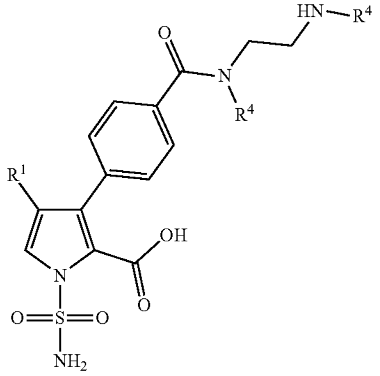

(IV)

wherein

X is independently selected from Cl, Br, I, $N_2^+$ or $OSO_2CF_3$;

$R^1$ is H or $C_{1-4}$ alkyl;

$R^2$ is a protecting group;

$R^3$ is independently selected from —$CH_2$-aryl or tert-butyl;

each $R^4$ is independently at each occurrence a $C_{1-4}$ alkyl;

$R^{8a}$ is $BF_3K$ or $B(OR^{9a})_2$; wherein either $R^{9a}$ is at each occurrence H or $C_{1-4}$ alkyl; or the two $R^{9a}$ substituents together form $(CR^aR^b)_n$; or the two $R^{9a}$ substituents together form —O(O)—$(CR^aR^b)$—$N(R_c)$—$(CR^aR^b)$—C(O)—;

$R^a$, $R^b$ and $R^c$ are independently selected at each occurrence from H and $C_{1-4}$ alkyl;

n is 2 or 3;

and

A is H or a cation.

In certain embodiments, step (b) of the first aspect may comprise the steps of (i) reacting the compound of formula (III) with a compound of formula (V) to form the compound of formula (VI):

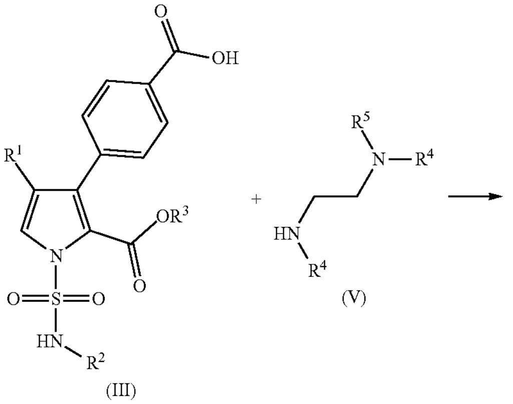

(III) (V)

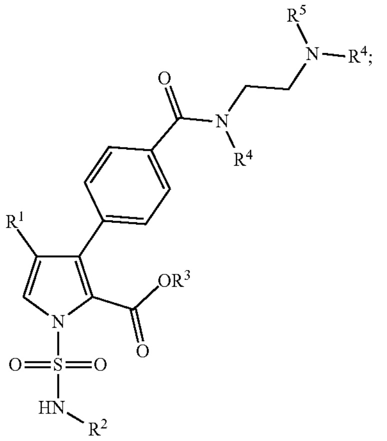

(VI)

and (ii) cleaving the $R^2$, $R^3$ and $R^5$ substituents from the compound of formula (VI) to form the compound of formula (IV) or a pharmaceutically acceptable salt thereof:

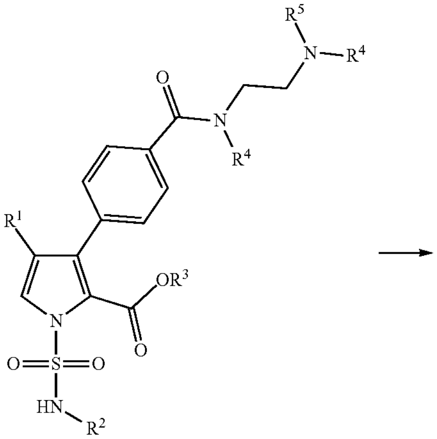

(VI)

-continued

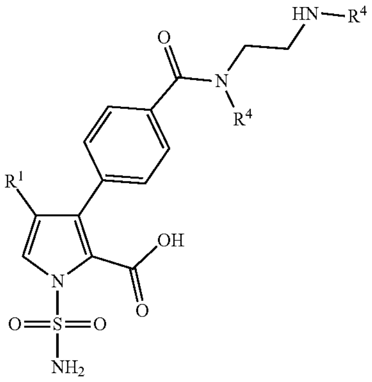

(IV)

wherein $R^5$ is a protecting group.

In certain embodiments, the compound of formula (I) is formed by reacting a compound of formula (VII) with a compound of formula (VIII) to form the compound of formula (I):

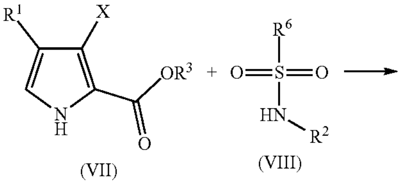

(VII) (VIII)

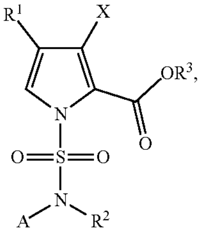

(I)

wherein $R^6$ is independently selected from F, Cl, Br, I, or

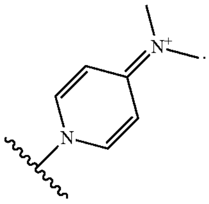 [SMILES: *n1ccc(=[N+](C)C)cc1]

In a second aspect of the invention is provided a method of forming a compound of formula (IV) or a pharmaceutically acceptable salt thereof, the method comprising:

(a) reacting the compound of formula (I) with a compound of formula (IX) to form a compound of formula (X);

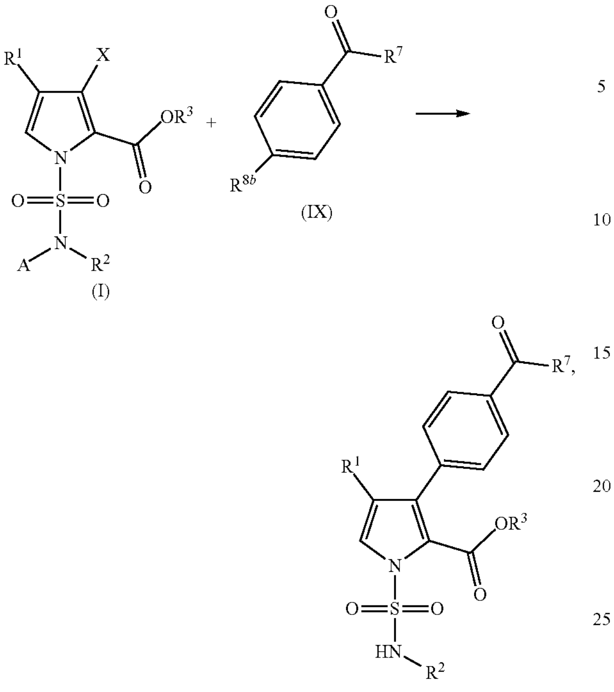

(I) (IX) (X)

(b) forming a compound of formula (IV) or a pharmaceutically acceptable salt thereof from the compound of formula (X):

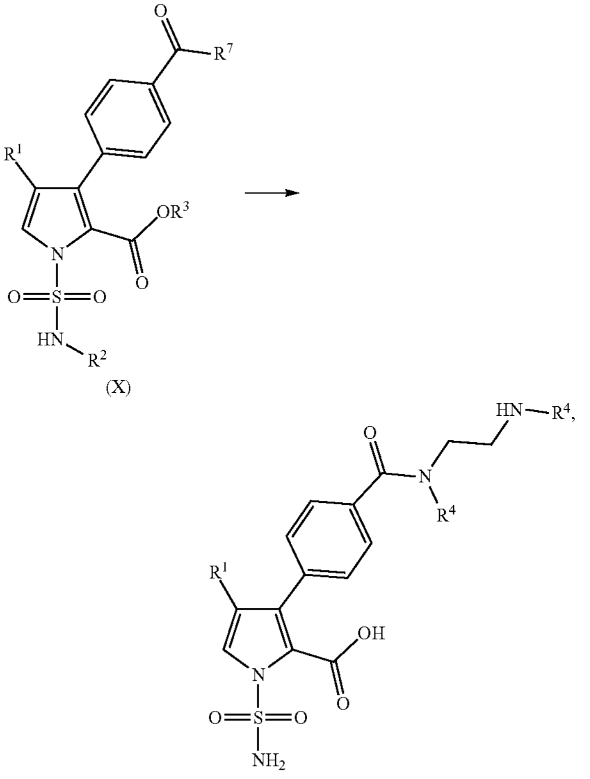

(X) (IV)

wherein

X is independently selected from Cl, Br, I or $OS(O)_2CF_3$;

$R^1$ is independently selected from H or $C_{1-4}$ alkyl;

$R^2$ is a protecting group;

$R^3$ is independently selected from —$CH_2$-aryl or tert-butyl;

each $R^4$ is independently at each occurrence a $C_{1-6}$ alkyl;

$R^5$ is a protecting group;

$R^7$ is independently selected from —$OR^{7a}$ or —$N(R^4)CH_2CH_2NR^4R^5$;

$R^{7a}$ is selected from —$C_{1-6}$ alkyl and —$CH_2$-aryl; $R^{8b}$ is independently selected from $BF_3K$ or $B(OR^{9b})_2$, wherein each $R^{9b}$ is H or $C_{1-4}$ alkyl; or the two $R^{9b}$ substituents together form $(CR^aR^b)_n$; or the two $R^{9a}$ substituents together form —C(O)—$(CR^aR^b)$—N$(R^c)$—$(CR^aR^b)$—C(O)—;

$R^a$, $R^b$ and $R^c$ are independently selected at each occurrence from H and $C_{1-4}$ alkyl;

n is 2 or 3;

and

A is independently selected from H or a cation.

In certain embodiments of the second aspect, when $R^7$ is —$OR^{7a}$, step (b) may comprise (i) cleaving the $R^{7a}$ substituent from the compound of formula (Xa) to form a compound of formula (III);

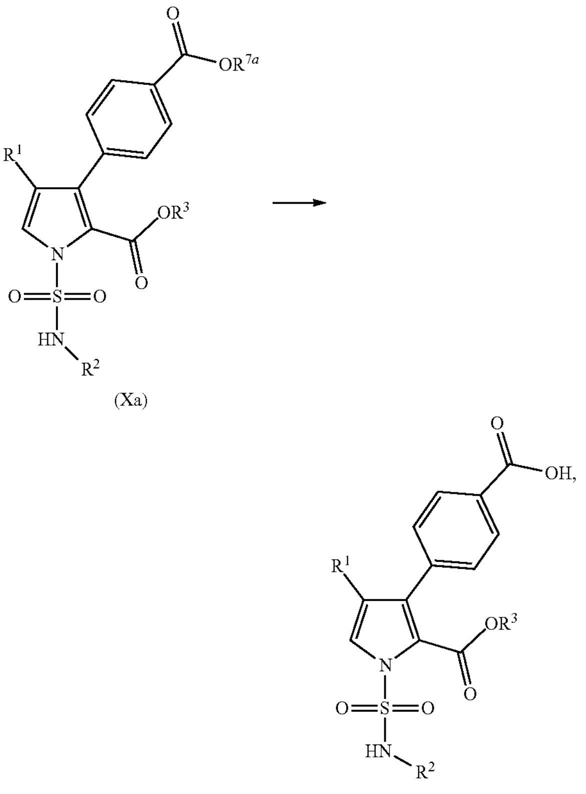

(Xa) (III)

and (ii) reacting the compound of formula (III) with a compound of formula (V) to form a compound of formula (VI):

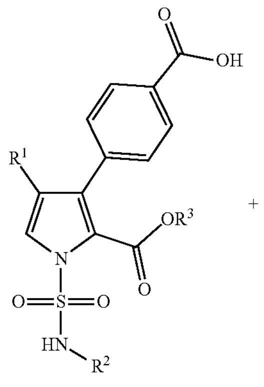

(III)

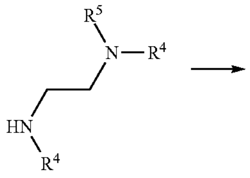

(V)

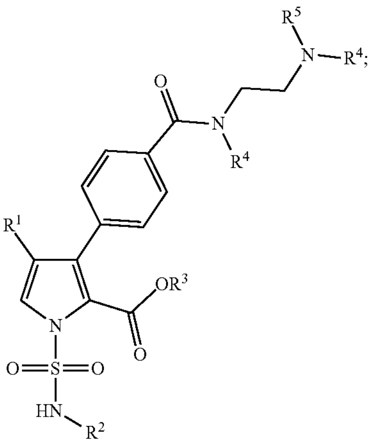

(VI)

and (iii) cleaving the $R^2$, $R^3$ and $R^5$ substituents from the compound of formula (VI) to form the compound of formula (IV) or a pharmaceutically acceptable salt thereof:

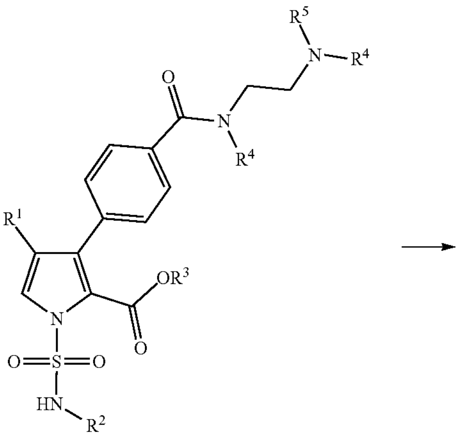

(VI)

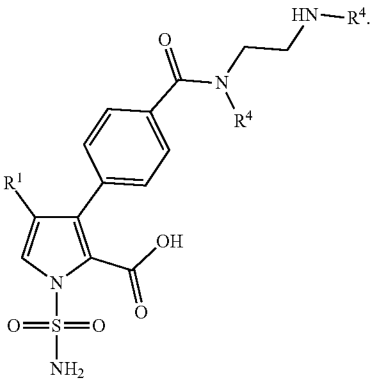

(IV)

In another embodiment of the second aspect, when $R^7$ is $-N(R^4)CH_2CH_2NR^4R^5$ (i.e. the compound of formula (X) is a compound of formula (VI)) step (b) may comprise cleaving the $R^2$, $R^3$ and $R^5$ substituents from the compound of formula (VI) to form the compound of formula (IV) or a pharmaceutically acceptable salt thereof:

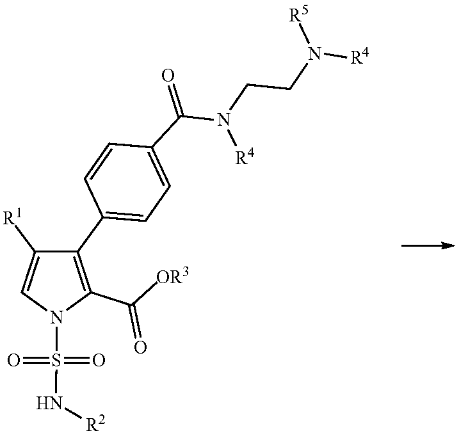

(VI)

-continued

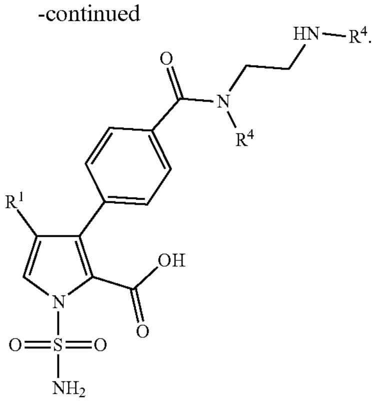

(IV)

This reaction may be as described above for the first aspect of the invention. Thus, in certain embodiments, the $R^2$, $R^3$ and $R^5$ substituents may be cleaved from the compound of formula (VI) via catalytic hydrogenation, e.g. as described for the first aspect of the invention.

In further embodiments, the process may comprise reacting a compound of formula (XI) with a compound of formula (V) to form the compound of formula (XII) (a specific example of a compound of formula (IX)):

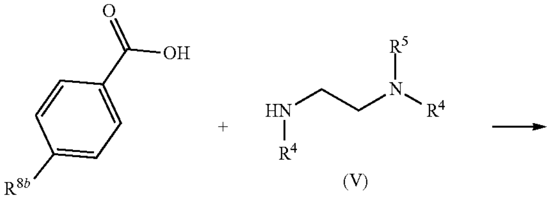

(XI) (V)

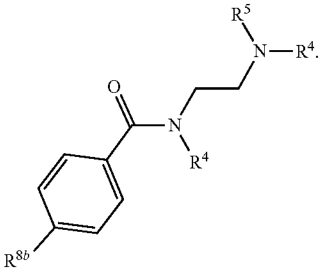

(XII)

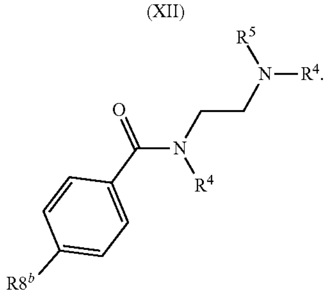

(XII)

The compound of formula (XII) can then be reacted with the compound of formula (I).

The compound of formula (I) may be produced as described above for the first aspect of the invention.

In a third aspect of the invention is provided a method of forming a compound of formula (IV) or a pharmaceutically acceptable salt thereof, the method comprising (a) reacting a compound of formula (XIII) with a compound of formula (XIV) to form a compound of formula (XV):

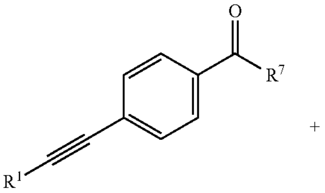

(XIII)

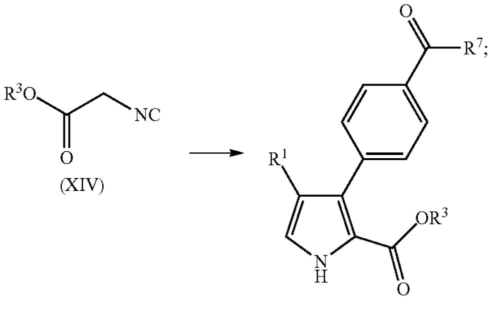

(XIV) (XV)

and (b) forming a compound of formula (IV) or a pharmaceutically acceptable salt thereof from the compound of formula (XV):

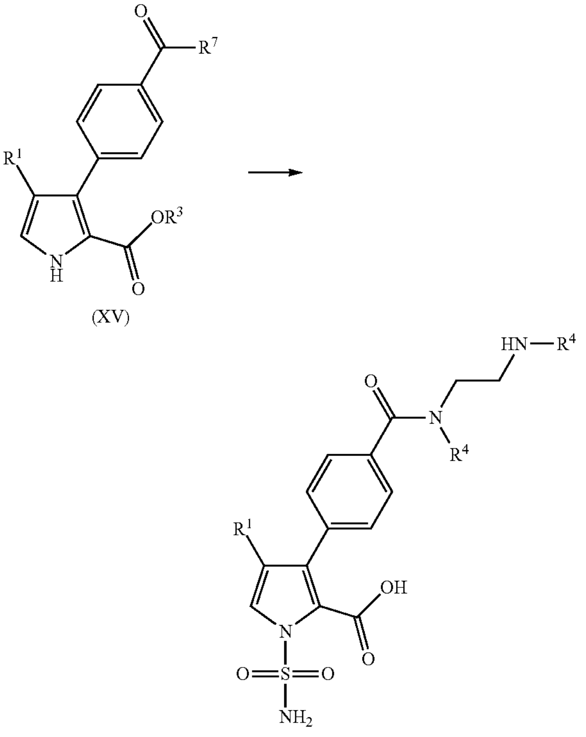

(XV) (IV)

wherein $R^1$ is independently selected from H or $C_{1-4}$ alkyl;

$R^3$ is independently selected from —$CH_2$-aryl or tert-butyl;

each $R^4$ is independently at each occurrence a $C_{1-6}$ alkyl;

$R^7$ is independently selected from —$OR^{7a}$, and —$N(R^4)CH_2CH_2NR^4R^5$; and $R^{7a}$ is $C_{1-6}$ alkyl or $CH_2$-aryl. In certain embodiments of the third aspect, when $R^7$ is —$N(R^4)CH_2CH_2NR^4R^5$, step (b) may comprise (i) reacting a compound of formula (XV) with a compound of formula (VIII) to form the compound of formula (VI):

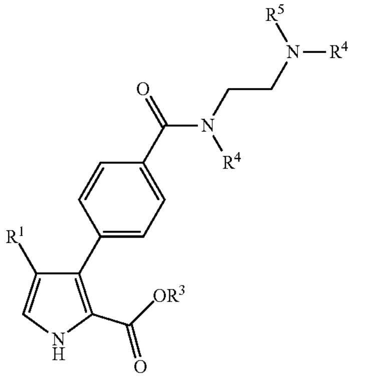

(XV)

+

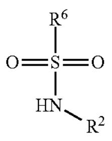

(VIII)

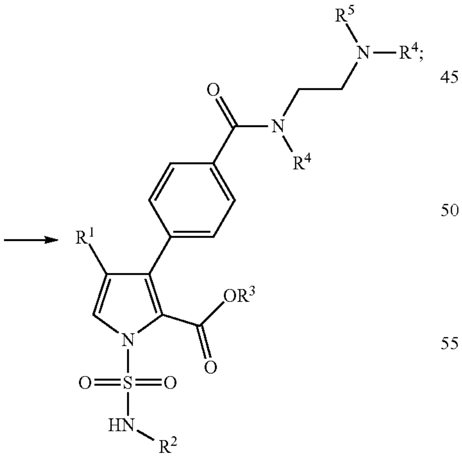

(VI)

and (ii) cleaving the $R^2$, $R^3$ and $R^5$ substituents from the compound of formula (VI) to form the compound of formula (IV) or a pharmaceutically acceptable salt thereof:

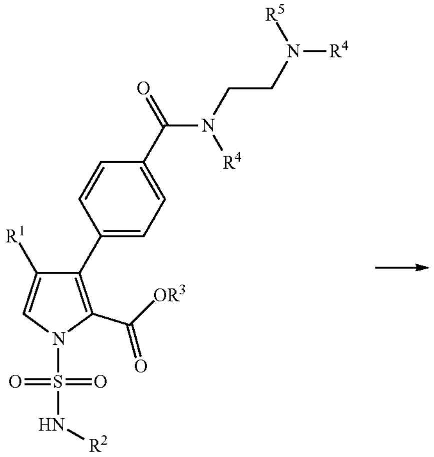

(VI)

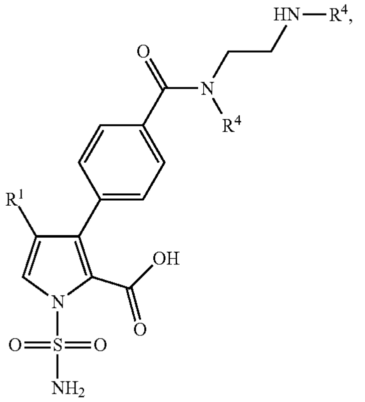

(IV)

wherein $R^5$ is a protecting group; and $R^6$ is independently selected from F, Cl, Br, I or

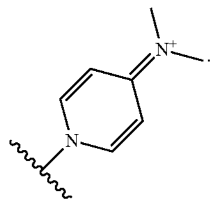 [SMILES: *n1ccc(=[N+](C)C)cc1]

In certain embodiments of the third aspect, when $R^7$ is —$N(R^4)CH_2CH_2NR^4R^5$, the compound of formula (XIIIa) may be formed by reacting a compound of formula (XVI) with a compound of formula (V):

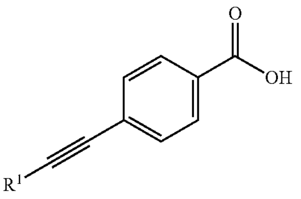

+

(XVI)

-continued

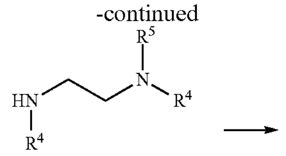

(V)

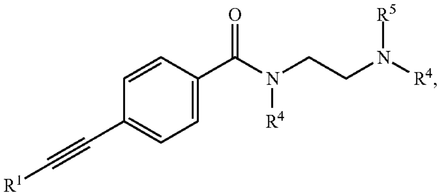

(XIIIa)

wherein $R^5$ is a protecting group.

In certain embodiments of the third aspect, when $R^7$ is —$OR^{7a}$, step (b) may comprise (i) cleaving the $R^{7a}$ substituent from the compound of formula (XVb) to form a compound of formula (XVII);

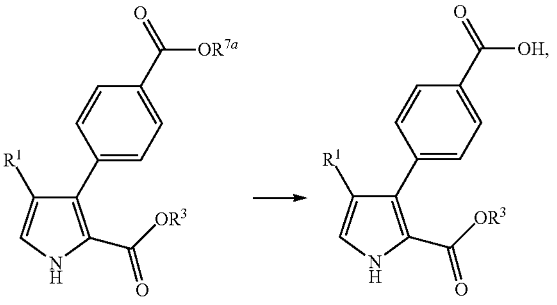

(XVb) (XVII)

(ii) reacting the compound of formula (XVII) with a compound of formula (V) to form a compound of formula (XVa):

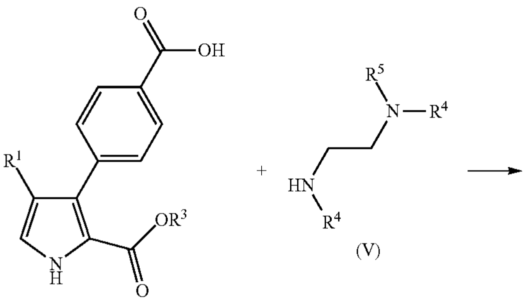

(XVII) (V)

-continued

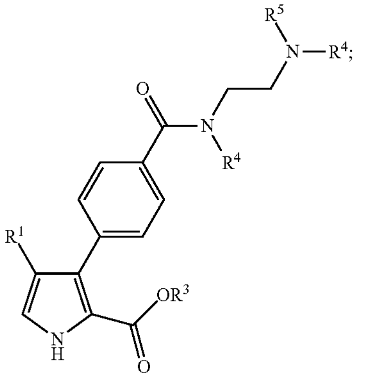

(XVa)

(iii) reacting a compound of formula (XVa) with a compound of formula (VIII) to form a compound of formula (VI):

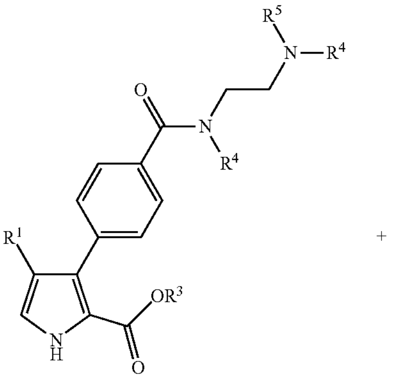

(XVa)

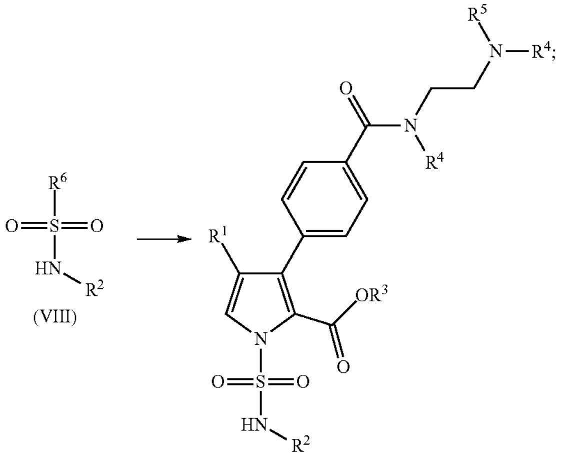

(VIII) (VI)

and (iv) cleaving the $R^2$, $R^3$ and $R^5$ substituents from the compound of formula (VI) to form the compound of formula (IV) or a pharmaceutically acceptable salt thereof:

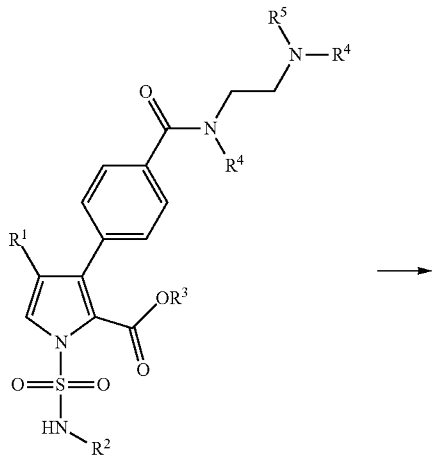

(VI)

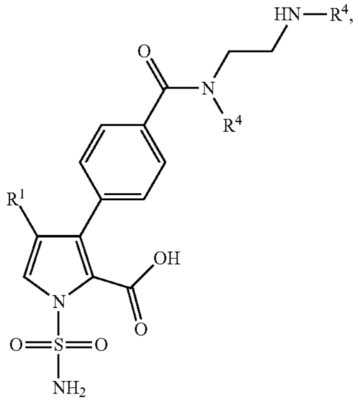

(IV)

wherein $R^5$ is a protecting group; and $R^6$ is independently selected from F, Cl, Br, I or

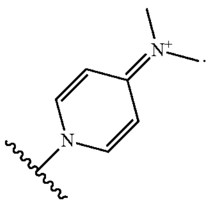 [SMILES: *n1ccc(=[N+](C)C)cc1]

In a fourth aspect of the invention is provided a method of forming a compound of formula (IV) or a pharmaceutically acceptable salt thereof, the method comprising:

(a) reacting a compound of formula (XVIII) with a compound of formula (XIX) to form a compound of formula (XV):

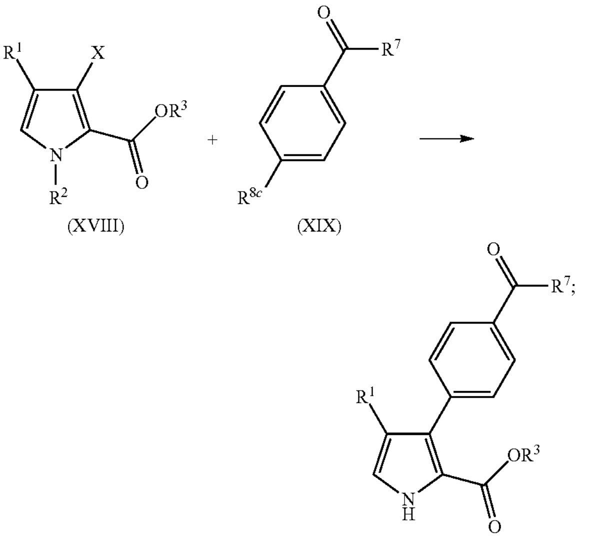

(XVIII) (XIX)

(XV)

and (b) forming a compound of formula (IV) or a pharmaceutically acceptable salt thereof from the compound of formula (XV):

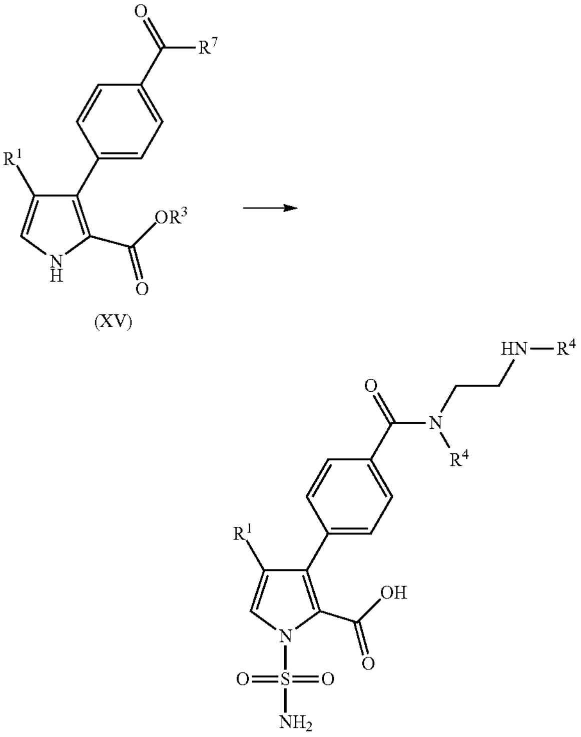

(XV)

(IV)

wherein $R^1$ is independently selected from H or $C_{1-4}$ alkyl;

$R^2$ is a protecting group;

$R^3$ is independently selected from —$CH_2$-aryl or tert-butyl;

each $R^4$ is independently at each occurrence a $C_{1-6}$ alkyl;

$R^7$ is independently selected from —$OR^{7a}$, and —$N(R^4)CH_2CH_2NR^4R^5$;

$R^{7a}$ is $C_{1-6}$ alkyl or $CH_2$-aryl; and $R^{8c}$ is $BF_3K$ or $B(OR^{9c})_2$; wherein either $R^{9c}$ is at each occurrence H or $C_{1-4}$ alkyl; or the two $R^{9c}$ substituents together form $(CR^aR^b)_n$; or the two $R^{9c}$ substituents together form —C(O)—$(CR^aR^b)$—N)($R^c$)—$(CR^aR^b)$—C(O)—.

In certain embodiments of the fourth aspect, step (b) may comprise converting the compound of formula (XV) to the compound of formula (IV) or pharmaceutically acceptable salt thereof according to any of the approaches described above for the third aspect.

$R^1$ may be H. $R^1$ may be $C_{1-4}$ alkyl.

$R^2$ may be independently selected at each occurrence from: tert-butyloxycarbonyl group (Boc), benzyloxycarbonyl (Cbz), tert-butyl ($^t$Bu), para-methoxybenzyl (PMB) and phthalimide. $R^2$ may be independently selected from tert-butyloxycarbonyl group (Boc) or benzyloxycarbonyl (Cbz). $R^2$ may be tert-butyloxycarbonyl group (Boc). $R^2$ may be benzyloxycarbonyl (Cbz).

$R^3$ may be —$CH_2$-aryl, e.g. benzyl or para-methoxybenzyl. $R^3$ may be benzyl. $R^3$ may be tert-butyl.

$R^4$ may be independently selected at each occurrence from methyl, ethyl, n-propyl or iso-propyl. $R^4$ may be methyl. $R^4$ may be ethyl.

$R^5$ may be independently selected from: tert-butyloxycarbonyl group (Boc) or benzyloxycarbonyl (Cbz). $R^5$ may be tert-butyloxycarbonyl group (Boc). $R^5$ may be benzyloxycarbonyl (Cbz).

It may be that $R^2$ is Cbz, $R^5$ is Cbz and $R^3$ is benzyl. It may be that $R^2$ is Boc, $R^5$ is Boc and $R^3$ is tert-butyl.

$R^2$, $R^3$ and $R^5$ may be selected such that each of $R^2$, $R^3$ and $R^5$ are cleaved under the same conditions. For example, each of $R^2$, $R^3$ and $R^5$ may be cleaved via catalytic hydrogenation (e.g. where $R^2$, $R^5$ and $R^3$ are benzyl and Cbz groups). Alternatively, each of $R^2$, $R^3$ and $R^5$ may be cleaved using a Bronsted acid (e.g. where $R^2$, $R^5$ and $R^3$ are tert-butyl and Boc groups).

Alternatively, it may be that $R^2$, $R^3$ and $R^5$ are selected such that they are all cleaved under different conditions or such that any two of $R^2$, $R^3$ and $R^5$ are cleaved under different conditions to the remaining one of $R^2$, $R^3$ and $R^5$. Thus, it may be that $R^2$, $R^3$ and $R^5$ may be selected such that $R^2$ and $R^5$ are not cleaved under conditions which result in the cleavage of $R^3$.

$R^7$ may be —$OR^{7a}$ e.g. —O—$CH_3$, —O—$CH_2CH_3$, —$CH_2CH_2CH_3$, or O—$C(CH_3)_3$. $R^7$ may be O—$C(CH_3)_3$. $R^7$ may be O-benzyl. Alternatively, $R^7$ may be $N(R^4)CH_2CH_2NR^4R^5$, e.g. $N(R^4)CH_2CH_2NR^4$Cbz or $N(R^4)CH_2CH_2NR^4$Boc.

$R^{8a}$, $R^{8b}$ or $R^{8c}$ may each independently be selected from $BF_3K$, —$B(OH)_2$, —$B(OCH_3)_2$,

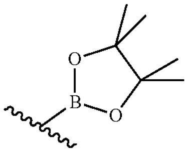

or

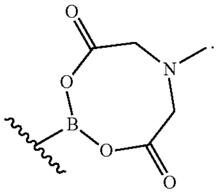

In certain embodiments of any of the first, second or third aspects, the compound of formula (IV) is a compound of formula (IVa):

(IVa)

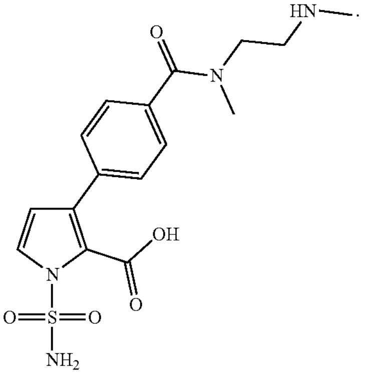

In certain embodiments of any of the first, second or third aspects, the compound of formula (V) is a compound of formula (Va):

(Va)

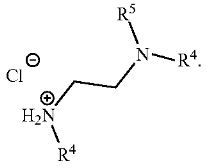

X may be independently selected from Cl, Br and I. X may be Cl. X may be Br.

It may be that $R^{9a}$ at each occurrence H. Thus, $R^{8a}$ may be $B(OH)_2$.

Reacting the compound of formula (I) with the compound of formula (II) may be conducted in the presence of an inorganic base, e.g. $NaHCO_3$. Reacting the compound of formula (I) with the compound of formula (II) may be conducted in a mixture of water and a $C_1$-$C_4$-alcohol, e.g. methanol. Reacting the compound of formula (I) with the compound of formula (II) may be conducted in a mixture of water and an aromatic hydrocarbon, e.g. toluene.

Reacting the compound of formula (III) with the compound of formula (V) may be conducted by first converting the compound of formula (III) to an acid chloride and subsequently reacting the acid chloride with the amine (V). Conversion of formula (III) to an acid chloride may be achieved using oxalyl chloride, e.g. in the presence of DMAP or DMF. Alternatively, it may be achieved using thionyl chloride, e.g. in the presence of DMAP or DMF. Reaction of the acid chloride with the amine (V) may be conducted in the presence of a base, e.g. an inorganic base, e.g. $NaHCO_3$.

Reacting the compound of formula (III) with the compound of formula (V) may be achieved using a suitable amide coupling reagent, e.g. propanephosphonic acid anhydride. The reaction may be conducted in the presence of a suitable organic base, e.g. triethylamine. The reaction may be conducted in acetonitrile.

Converting the compound of formula (VI) to the compound of formula (IV) may be achieved using a palladium catalysed hydrogenation, e.g. using $H_2$ and Pd/C. The reaction may be conducted in the presence of $NH_3$ and methanol. The reaction may be conducted in 1,4-dioxane. The reaction may be conducted in a polyfluorinated $C_1$-$C_4$-alcohol, e.g. 2,2,2-trifluoroethanol or 1,1,1,3,3,3-hexafluoro-2-propanol.

Reacting a compound of formula (VII) with a compound of formula (VIII) is typically conducted in the presence of a base, e.g. NaH. The reaction may be performed in THF.

A may be Na.

It may be that $R^{8b}$ is

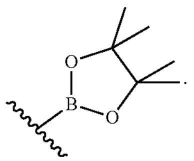 [SMILES: *B1OC(C)(C)C(C)(C)O1]

Reacting the compound of formula (I) with a compound of formula (IX) will typically be conducted in the presence of palladium, e.g. Pd/C, XPhos Pd G2, $Pd(PPh_3)_4$, Pd(dppf)$Cl_2$. The reaction may be conducted in the presence of XPhos Pd G2, $Pd(PPh_3)_4$, or Pd(dppf)$Cl_2$. The reaction may be conducted in the presence of an inorganic base, e.g. $K_3PO_4$. The reaction may be conducted in 1,4-dioxane.

It may be that $R^7$ is selected from —O—$C_{1-6}$-alkyl or —O—$CH_2$-aryl. It may be that $R^7$ is selected from —O-tert-butyl and O-benzyl. Where $R^7$ is selected from —O—$C_{1-6}$-alkyl or —O—$CH_2$-aryl, $R^2$ and $R^3$ are preferably selected so that they are not cleaved under the same conditions as $R^7$. It may be that $R^7$ is —O—$C_{1-6}$-alkyl, e.g. —O-tert-butyl. Where $R^7$ is —O—$C_{1-6}$-alkyl, e.g. —O-tert-butyl, $R^2$ is preferably Cbz and $R^3$ is preferably benzyl. It may be that $R^7$ is —O—$CH_2$-aryl, e.g. —O-benzyl. Where $R^7$ is —O—$CH_2$-aryl, e.g. —O-benzyl, $R^2$ is preferably Boc and $R^3$ is preferably tBu.

Where $R^7$ is —O-tert-butyl, the conversion of the compound of formula (Xa) to form a compound of formula (III) may be conducted in the presence of a Bronsted acid, e.g. TFA.

The conversion may be conducted in DCM.

Where $R^7$ is —O-benzyl, the conversion of the compound of formula (Xa) to form a compound of formula (III) may be achieved using a palladium catalysed hydrogenation, e.g. using $H_2$ and Pd/C. The reaction may be conducted in the presence of $NH_3$ and methanol. The reaction may be conducted in 1,4-dioxane.

$R^7$ may be $N(R^4)CH_2CH_2NR^4R^5$, e.g. $N(R^4)CH_2CH_2NR^4$Cbz or $N(R^4)CH_2CH_2NR^4$Boc. $R^7$ may be $N(Me)CH_2CH_2NMeR^5$, e.g. $N(Me)CH_2CH_2NMe$Cbz or $N(Me)CH_2CH_2NMe$Boc.

Reacting a compound of formula (XI) with a compound of formula (V) may be conducted by first converting the compound of formula (XI) to an acid chloride and subsequently reacting the acid chloride with the amine (V). Conversion of formula (XI) to an acid chloride may be achieved using oxalyl chloride, e.g. in the presence of DMAP or DMF. Alternatively, it may be achieved using thionyl chloride, e.g. in the presence of DMAP or DMF. Reaction of the acid chloride with the amine (V) may be conducted in the presence of a base, e.g. an inorganic base, e.g. $NaHCO_3$.

Reacting a compound of formula (XIII) with a compound of formula (XIV) may be conducted in the presence of a silver salt or a copper salt. The reaction may be performed in the presence of a silver salt, e.g. $Ag_2CO_3$. The reaction may be performed in the presence of a copper salt. The copper salt may be a Cu(I) salt, e.g. $Cs_2CO_3$/CuBr, $Cu_2O$/1,10-phenanthroline, or Cu(I) thiophene-2-carboxylate. The copper salt may be a Cu(II) salt, e.g. $Cu(OAc)_2$. The reaction may be conducted in 1,4-dioxane.

Reacting a compound of formula (XVIII) with a compound of formula (XIX) may be conducted in the presence of palladium, e.g. Pd/C, XPhos Pd G2, $Pd(PPh_3)_4$, Pd(dppf)$Cl_2$. The reaction may be conducted in the presence of XPhos Pd G2, $Pd(PPh_3)_4$, or Pd(dppf)$Cl_2$. The reaction may be conducted in the presence of an inorganic base, e.g. $K_3PO_4$. The reaction may be conducted in 1,4-dioxane/water.

Reacting a compound of formula (XV) with a compound of formula (VIII) is typically conducted in the presence of a base, e.g. NaH. The reaction may be performed in THF.

Reacting a compound of formula (XVI) with a compound of formula (V) may be performed in the presence of HBTU. The reaction may be performed in DCM.

DETAILED DESCRIPTION

The chemical terms used in the specification have their generally accepted meanings in the art.

The term "halo" refers to fluoro, chloro, bromo and iodo.

The term "alkyl" refers to a linear or branched saturated monovalent hydrocarbon chain. For example, $C_1$-$C_6$-alkyl may refer to methyl, ethyl, n-propyl, iso-propyl, n-butyl, sec-butyl, tert-butyl, n-pentyl and n-hexyl. The alkyl groups may be unsubstituted or substituted by one or more substituents.

The term "alkylene" refers to a linear saturated divalent hydrocarbon chain. The alkylene groups may be unsubstituted or substituted by one or more substituents.

The term "haloalkyl" refers to a hydrocarbon group substituted with at least one halogen atom independently chosen at each occurrence from: fluorine, chlorine, bromine and iodine. The halogen atom may be present at any position on the hydrocarbon chain. For example, $C_1$-$C_6$-haloalkyl may refer to chloromethyl, fluoromethyl, trifluoromethyl, chloroethyl e.g. 1-chloroethyl and 2-chloroethyl, trichloroethyl e.g. 1,2,2-trichloroethyl, 2,2,2-trichloroethyl, fluoroethyl e.g. 1-fluoroethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be a fluoroalkyl group, i.e. a hydrocarbon chain substituted with at least one fluorine atom. Thus, a haloalkyl group may have any amount of halogen substituents. The group may contain a single halogen substituent, it may have two or three halogen substituents, or it may be saturated with halogen substituents.

The term "alkenyl" refers to a branched or linear hydrocarbon group containing at least one double bond. The double bond(s) may be present as the E or Z isomer. The double bond may be at any possible position of the hydrocarbon chain; for example, "$C_2$-$C_6$-alkenyl" may refer to ethenyl, propenyl, butenyl, butadienyl, pentenyl, pentadienyl, hexenyl and hexadienyl. The alkenyl groups may be unsubstituted or substituted by one or more substituents.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. The alkynyl groups may be unsubstituted or substituted by one or more substituents.

The term "cycloalkyl" refers to a saturated hydrocarbon ring system containing, for example, 3, 4, 5 or 6 carbon atoms. For example, "$C_3$-$C_6$-cycloalkyl" may refer to cyclopropyl, cyclobutyl, cyclopentyl, cyclohexyl. The cycloalkyl groups may be unsubstituted or substituted by one or more substituents.

The term "heterocycloalkyl" may refer to a monocyclic or bicyclic saturated or partially saturated group having the indicated number of atoms in the ring system and comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 6 members. The double bond will typically be between two carbon atoms but may be between a carbon atom and a nitrogen atom. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine. A heterocycloalkyl group may be unsubstituted or substituted by one or more substituents.

The term "aryl" may refer to any aromatic carbocyclic ring system (i.e. a ring system containing $2(2n+1)\pi$ electrons). Aryl groups may have from 6 to 12 carbon atoms in the ring system. Aryl groups will typically be phenyl groups. Aryl groups may be naphthyl groups or biphenyl groups.

The term "heteroaryl" or "heteroaromatic" means any aromatic (i.e. a ring system containing $2(2n+1)\pi$ electrons) 5-10 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 14 heteroatoms independently selected from O, S and N; and 6-membered heteroaryl groups in which the heteroaromatic ring is substituted with 1-3 (e.g. 1-2) nitrogen atoms; 9-membered bicyclic heteroaryl groups in which the heteroaromatic system is substituted with 1-4 heteroatoms independently selected from O, S and N; 10-membered bicyclic heteroaryl groups in which the heteroaromatic system is substituted with 1-4 nitrogen atoms. Specifically, heteroaryl groups may be independently selected from: pyrrole, furan, thiophene, pyrazole, imidazole, oxazole, isoxazole, triazole, thiazole, isothiazole, oxadiazole, thiadiazole, tetrazole, pyridine, pyridazine, pyrimidine, pyrazine, triazine, indole, isoindole, benzofuran, isobenzofuran, benzothiophene, indazole, benzimidazole, benzoxazole, benzothiazole, benzisoxazole, benzofurazine, purine, quinoline, isoquinoline, cinnoline, quinazoline, quinoxaline, pteridine, phthalazine, naphthyridine, carbazole, phenazine, benzoisoquinoline, pyridopyrazine, thiophenofuran, 2H-furopyrazine, 5H-pyridooxazine, 1H-pyrazoloxazole, 4H-imidazothiazole, pyrazinopyridazine, imidazothiazole, imidazotriazine.

The term "protecting group" as used herein is given its ordinary meaning which is readily understandable to those of skill in the art. It is used herein to refer to a group suitable for protecting a nitrogen or oxygen. Exemplary protecting groups suitable for protecting a nitrogen include tert-butyloxycarbonyl group (Boc group), benzyloxycarbonyl group (Cbz), tert-butyl group ($^t$Bu), para-methoxybenzyl (PMB) and phthalimide. Exemplary protecting groups suitable for protecting an oxygen include benzyl group (Bn) and tert-butyl group ($^t$Bu)

Where multiple protecting groups are present on the same compound, the protecting groups may or may not be orthogonal to one another (i.e. if a first protecting group can be removed without also removing a second protecting group, the two groups are said to be orthogonal). In the methods of the present invention, the protecting groups are typically not orthogonal to one another.

Compounds disclosed herein containing one or more asymmetric carbon atoms can exist as two or more stereoisomers. Where a compound contains a double bond such as a C═C or C═N group, geometric cis/trans (or Z/E) isomers are possible. Where structural isomers are interconvertible via a low energy barrier, tautomeric isomerism ('tautomerism') can occur.

This can take the form of proton tautomerism in compounds disclosed herein containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds produced in methods of the invention, including compounds exhibiting more than one type of isomerism, and mixtures of one or more thereof.

The compounds produced in methods of the invention may be obtained, stored and/or used in the form of a pharmaceutically acceptable salt. Suitable salts include, but are not limited to, salts of acceptable inorganic acids such as hydrochloric, sulfuric, phosphoric, nitric, carbonic, boric, sulfamic, and hydrobromic acids, or salts of agronomically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Suitable salts also include salts of inorganic and organic bases, e.g. counterions such as Na, Ca, K, Li, Mg, ammonium, trimethylsulfonium. The compounds may also be obtained, stored and/or used in the form of an N-oxide. Also included are acid addition salts or base salts wherein the counter ion is optically active; for example, d-lactate or 1-lysine, or racemic; for example, dl-tartrate or dl-arginine.

Pharmaceutically acceptable salts of compounds produced in the methods of the invention may be prepared by for example, one or more of the following methods:

(i) by reacting the compound with the desired acid or base;

(ii) by removing an acid- or base-labile protecting group from a suitable precursor of the compound of the invention or by ring-opening a suitable cyclic precursor, for example, a lactone or lactam, using the desired acid or base; or (iii) by converting one salt of the compound to another by reaction with an appropriate acid or base or by means of a suitable ion exchange column.

These methods are typically carried out in solution. The resulting salt may precipitate out and be collected by filtration or may be recovered by evaporation of the solvent. The degree of ionisation in the resulting salt may vary from completely ionised to almost non-ionised.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallisation and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see for example, “Stereochemistry of Organic Compounds” by E. L. Eliel and S. H. Wilen (Wiley, 1994).

Methods for the determination of stereochemistry and the separation of stereoisomers are well-known in the art (see discussion in “Advanced Organic Chemistry”, 7th edition J. March, John Wiley and Sons, New York, 2013).

The present invention also encompasses compounds produced in methods of the invention as defined herein which comprise one or more isotopic substitutions. For example, H may be in any isotopic form, including $^{1}H$, $^{2}H(D)$, and $^{3}H$ (T); C may be in any isotopic form, including $^{12}C$, $^{13}C$, and $^{14}C$; and O may be in any isotopic form, including $^{16}O$ and $^{18}O$; and the like. Similarly, isotopic variants of N, S and P may be utilised.

It may be that the steps described above as individual steps are performed in tandem. In other words, it may be that a reaction product from one step is not isolated and purified before the next step. It may be that the reagents for one step are added into the reaction mixture obtained in the immediately preceding step once the reaction of the first step is complete. For example, where a reaction sequence involves a Suzuki reaction (e.g. step a) or the first aspect of the invention) followed by a hydrogenolysis, it may be that $H_2$ is simply added to the reaction mixture from the Suzuki reaction once that reaction is complete.

Throughout the description and claims of this specification, the words “comprise” and “contain” and variations of them mean “including but not limited to”, and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The reader’s attention is directed to all papers and documents which are filed concurrently with or previous to this specification in connection with this application and which are open to public inspection with this specification, and the contents of all such papers and documents are incorporated herein by reference.

EXAMPLES

The following examples represent specific methods of producing the compound of formula (IV).

General Experimental

The following abbreviations have been used:

Bn—benzyl
Cbz—carboxybenzyl
DCM—dichloromethane
DIPEA—N,N-diisopropylethylamine
DMAP—N,N-dimethyl-4-aminopyridine
DMF—N,N-dimethylformamide
DMSO—dimethyl sulfoxide
HBTU—N,N,N',N'-tetramethyl-O-(1H-benzotriazol-1-yl)uronium hexafluorophosphate
HFIP—1,1,1,3,3,3-hexafluoro-2-propanol
T3P—propanephosphonic acid anhydride
TFA—trifluoroacetic acid
TFE—2,2,2-trifluoroethanol
THF—tetrahydrofuran
XPhos—2-dicyclohexylphosphino-2',4',6'-triisopropylbiphenyl
XPhos Pd G2—chloro(2-dicyclohexylphosphino-2',4',6'-triisopropyl-1,11-biphenyl)[2-(2'-amino-1,11-biphenyl)]palladium(11)

Analytical Methods

All $^{1}H$ NMR spectra were obtained on a Bruker AVI 500 with 5 mm QNP. Chemical shifts (δ) are expressed in parts per million (ppm) and are referenced to the solvent. Coupling constants (J) are expressed in Hertz (Hz).

LC-MS were obtained on a Waters Alliance ZQ (Methods A and B) or Waters Acquity H-class UPLC (Method C) using the methods detailed below. Wavelengths were 254 and 210 nm.

Method A

Column: YMC-Triart C18, 2.0×50 mm, 5 μm. Flow rate: 0.8 mL/min. Injection volume: 6 μL.

Mobile Phase: A=water, B=acetonitrile, C=1:1 water:acetonitrile+1.0% formic acid.

| Time | % A | % B | % C |
|---|---|---|---|
| Initial | 90 | 5 | 5 |
| 4.0 | 0 | 95 | 5 |
| 6.0 | 0 | 95 | 5 |

Method B

Column: YMC-Triart C18, 2.0×50 mm, 5 μm. Flow rate: 0.8 mL/min. Injection volume: 6 μL.

Mobile Phase: A=water, B=acetonitrile, C=1:1 water:acetonitrile+1.0% formic acid.

| Time | % A | % B | % C |
|---|---|---|---|
| Initial | 95 | 0 | 5 |
| 2.0 | 95 | 0 | 5 |
| 12.0 | 0 | 95 | 5 |
| 14.0 | 0 | 95 | 5 |

Method C

Column: CSH C18, 2.1×50 mm, 1.7 μm. Flow rate: 1.0 mL/min. Injection volume: 5 μL.

Mobile Phase: A=water+0.1% formic acid, B=acetonitrile+0.1% formic acid.

| Time | % A | % B |
|---|---|---|
| Initial | 98 | 2 |
| 0.2 | 98 | 2 |
| 2.5 | 2 | 98 |
| 3.0 | 2 | 98 |
| 3.1 | 98 | 2 |
| 3.5 | 98 | 2 |

Intermediate Synthesis

Intermediate 1: Benzyl N-methyl-N-[2-(methylamino)ethyl]carbamate

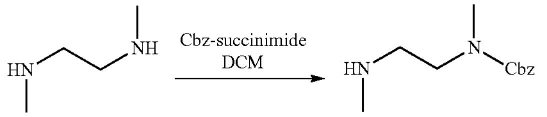

To a cooled (0° C.) solution of N,N'-dimethylethane-1,2-diamine (130 mL, 1.20 mol) in DCM (500 mL) under argon was added dropwise a solution of N-(benzyloxycarbonyloxy) succinimide (60 g, 241 mmol) in DCM (500 mL) over ~90 minutes and allowed to stir for a further 2.5 hours at room temperature.

Workup A: Isolation of HCl Salt

The reaction mixture was concentrated to dryness, the residue redissolved in ethyl acetate (1500 mL) and washed with water (2×750 mL). The aqueous phase was extracted with ethyl acetate (500 mL), the combined organics washed with brine (500 mL) then dried over $MgSO_4$, filtered and concentrated to dryness to give a colourless oil. The oil was redissolved in ethyl acetate (500 mL), cooled to 0° C. and 4 M HCl in 1,4-dioxane (78.2 mL, 313 mmol) was added dropwise to the stirred solution. The resulting precipitate was isolated by filtration, washed with ethyl acetate followed by petroleum ether to give the desired HCl salt as a white solid (49.1 g, 79%).

$^1H$ NMR (500 MHz, DMSO-$d_6$) δ 9.19-8.97 (m, 2H), 7.42-7.30 (m, 5H), 5.08 (s, 2H), 3.60-3.51 (m, 2H), 3.03 (br s, 2H), 2.94-2.85 (m, 3H), 2.57-2.48 (m, 3H).

Workup B: Distillation of Free Base

The reaction mixture was concentrated under reduced pressure followed by the addition of water (300 mL) and extraction into diethyl ether (2×300 mL). The combined organic phases were dried over $MgSO_4$, filtered and concentrated to dryness. The resulting yellow oil was purified by short path distillation (product distils at 116° C. at 0.45 mbar) to give the desired free base as a colourless oil (36 g, 64%).

$^1H$ NMR (500 MHz, $CDCl_3$) δ 7.39-7.28 (m, 5H), 5.13 (s, 2H), 3.41 (br s, 2H), 2.96 (s, 3H), 2.80-2.69 (m, 2H), 2.49-2.36 (m, 3H).

Intermediate 2: Benzyl N-chlorosulfonylcarbamate

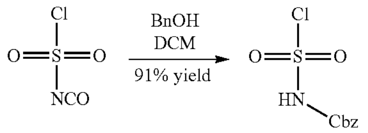

Chlorosulfonyl isocyanate (30 mL, 346 mmol) was added to DCM (500 mL) and cooled to 0° C. under a nitrogen atmosphere. Once cooled, a solution of benzyl alcohol (37.4 g, 35.7 mL, 346 mmol) in DCM (100 mL) was slowly added to the mixture then the reaction allowed to warm up to room temperature and stirred for 1 hour. The mixture was evaporated to approximately 50% of solvent volume and, with vigorous stirring, petroleum ether was added until a solid crashed out. The resulting slurry was stirred for 20 minutes before being filtered and dried under a stream of nitrogen for 1 hour to give the desired product as a white solid (79 g, 91%).

$^1H$ NMR (500 MHz, $CDCl_3$) δ 8.88 (br s, 1H), 7.40 (s, 5H), 5.31 (s, 2H).

Example 1—Synthesis of 3-[4-[Methyl-[2-(methylamino)ethyl]carbamoyl]phenyl]-1-sulfamoyl-pyrrole-2-carboxylic acid

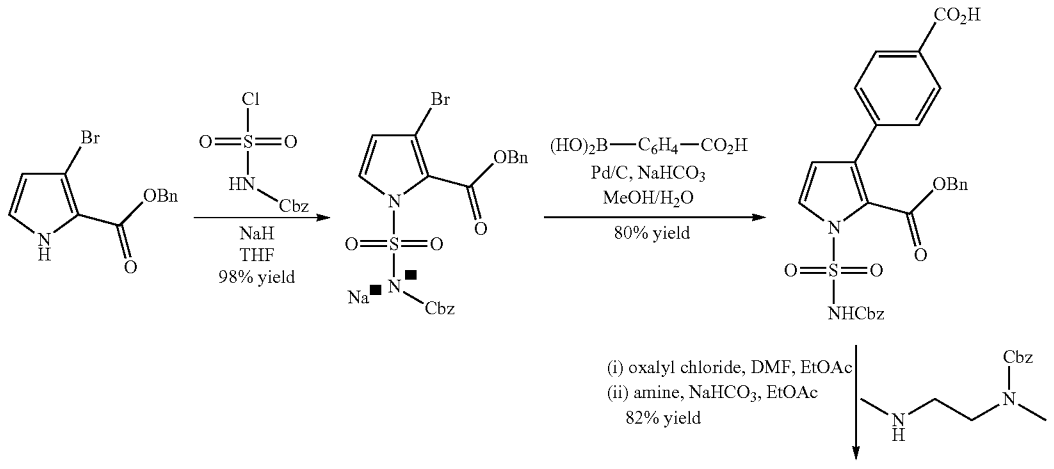

-continued

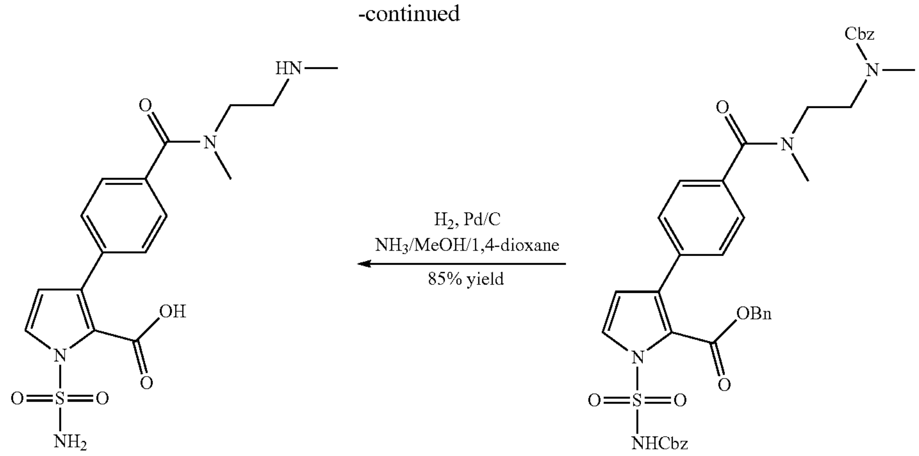

Step 1: Sodium benzyloxycarbonyl-(2-benzyloxy-carbonyl-3-bromo-pyrrol-1-yl)sulfonyl-azanide A suspension of sodium hydride (60% in mineral oil, 23.6 g, 589 mmol) in anhydrous THF (200 mL) was cooled to −10° C. under a nitrogen atmosphere followed by the dropwise addition of a solution of benzyl 3-bromo-1H-pyrrole-2-carboxylate (55 g, 196 mmol) in anhydrous THF (200 mL) over a period of 45 minutes ensuring that the temperature was maintained below −5° C. The reaction mixture was allowed to warm to room temperature and stirred for 1 hour before recooling to −10° C. To the reaction mixture was added benzyl N-chlorosulfonylcarbamate (53.9 g, 216 mmol) portionwise over a period of 30 minutes ensuring that the temperature was maintained below −5° C. The reaction mixture was allowed to warm to room temperature and stirred for 2 hours, then recooled to −10° C. and quenched by the dropwise addition of 50:50 water:brine (250 mL). The mixture was extracted into ethyl acetate (3×100 mL) and the combined organic phases washed with brine (200 mL), dried over $MgSO_4$, the solution decanted and concentrated to dryness. The residue was triturated in diethyl ether (200 mL), filtered and sucked dry, then retriturated in diethyl ether (250 mL), filtered and sucked dry to give the desired product as a white solid (99.8 g, 98%).

$^1$H NMR (500 MHz, DMSO-$d_6$) δ 7.56-7.52 (m, 2H), 7.36-7.26 (m, 9H), 6.17 (d, J=3.4 Hz, 1H), 5.23 (s, 2H), 4.85 (s, 2H).

Step 2: 4-[2-Benzyloxycarbonyl-1-(benzyloxycarbonylsulfamoyl)pyrrol-3-yl]benzoic acid A solution of sodium benzyloxycarbonyl-(2-benzyloxy-carbonyl-3-bromo-pyrrol-1-yl)sulfonyl-azanide (20.0 g, 38.8 mmol) and 4-carboxyphenylboronic acid (7.08 g, 42.7 mmol) in methanol (100 mL) was degassed with nitrogen for 30 minutes followed by the addition of 10% palladium on activated carbon (Type 58, standard, reduced, nominally 50% water wet, 2.07 g, 0.97 mmol) and the mixture evacuated under vacuum with the atmosphere replaced with nitrogen three times. A degassed (30 minutes, nitrogen) solution of sodium bicarbonate (6.52 g, 77.6 mmol) in water (100 mL) was added slowly to the reaction mixture. Upon complete addition the reaction mixture was evacuated under vacuum and the atmosphere replaced with nitrogen before heating to 80° C. overnight. After allowing to cool to room temperature, the reaction mixture was filtered through a pad of Celite® (pre-conditioned with water), the pad washed with water (2×100 mL), and the combined filtrates extracted with diethyl ether (2×100 mL). The aqueous layer was added as a slow steady stream into a stirred mixture of acetic acid (30 mL) and water (270 mL) at 50° C. over a period of approximately 1 hour. After complete addition, the resulting slurry was stirred for 10 minutes at 50° C. then allowed to cool to room temperature and stirred for a further 1 hour. The precipitated solid was isolated by filtration, washed with water (2×50 mL) and dried at 60° C. under vacuum to give the desired product as a white solid (17.0 g, 80%).

$^1$H NMR (500 MHz, DMSO-$d_6$) δ 7.84 (d, J=8.2 Hz, 2H), 7.43-7.39 (m, 3H), 7.36-7.30 (m, 5H), 7.29-7.25 (m, 5H), 6.42 (d, J=2.6 Hz, 1H), 5.19 (s, 2H), 5.00 (s, 2H). LC-MS (Method A): $R_T$=3.42 min, m/z=533.8 $[M-H]^-$.

Step 3: Benzyl 3-[4-[2-[Benzyloxycarbonyl(methyl)amino]ethyl-methyl-carbamoyl]phenyl]-1-(benzyloxycarbonylsulfamoyl)pyrrole-2-carboxylate To a suspension of 4-[2-benzyloxycarbonyl-1-(benzyloxycarbonylsulfamoyl)pyrrol-3-yl]benzoic acid (15.0 g, 28.0 mmol) in ethyl acetate (150 mL) was added DMF (43 μL, 0.56 mmol) followed by the dropwise addition of oxalyl chloride (2.68 mL, 30.9 mmol). The resulting suspension was heated to 40° C. for 1 hour, then concentrated under reduced pressure to approximately half the volume. To this was then added solid sodium bicarbonate (5.19 g, 61.7 mmol) followed by the dropwise addition of a solution of benzyl N-methyl-N-[2-(methylamino)ethyl]carbamate (7.49 g, 33.7 mmol) in ethyl acetate (75 mL). After stirring at room temperature overnight the reaction mixture was acidified by the addition of 2M aqueous HCl (100 mL). The layers were separated and the organic phase washed with 2M aqueous HCl (100 mL), brine (100 mL), dried over $MgSO_4$, filtered and concentrated to ~100 mL volume under reduced pressure. This was heated to 60° C. followed by the slow addition of cyclohexane (200 mL). After stirring at 60° C. for 15 minutes the resulting suspension was allowed to cool to room temperature and stirred overnight. The precipitated solid was isolated by filtration, washed with cyclohexane (2×50 mL) and sucked dry to give the desired product as a white solid (17.0 g, 82%).

$^1$H NMR (500 MHz, DMSO-$d_6$) δ 7.52-7.09 (m, 20H), 6.51-6.34 (m, 1H), 5.20 (br s, 2H), 5.14-4.78 (m, 4H), 3.71-2.53 (m, 10H). LC-MS (Method A): $R_T$=3.70 min, m/z=739.9 $[M+H]^+$.

Step 4: 3-[4-[Methyl-[2-(methylamino)ethyl]carbamoyl]phenyl]-1-sulfamoyl-pyrrole-2-carboxylic acid (Compound IVa)

10% Palladium on activated carbon (Type 58, standard, reduced, nominally 50% water wet, 720 mg, 0.34 mmol) was added to a purged (evacuated under vacuum then replaced with nitrogen three times) solution of benzyl 3-[4-[2-[benzyloxycarbonyl(methyl)amino]ethyl-methyl-carbamoyl]phenyl]-1-(benzyloxycarbonylsulfamoyl)pyrrole-2-carboxylate (5.00 g, 6.77 mmol) in a mixture of methanol (17.5 mL) and 1,4-dioxane (17.5 mL). The reaction mixture was purged three times with vacuum/nitrogen and 7M ammonia in methanol (7.73 mL, 54.1 mmol) added. The reaction mixture was purged once with vacuum, the atmosphere replaced with hydrogen (1 atm) and stirred overnight at room temperature. The reaction mixture was filtered through a Celite® pad (pre-conditioned with 7M ammonia in methanol) and the pad washed with further 7M ammonia in methanol (50 mL). The combined filtrates were diluted with methanol (50 mL) and concentrated under reduced pressure to remove approximately 50 mL of solvent a total of three times, then stirred at room temperature for 1 hour. The resulting precipitate was isolated by filtration and dried at 60° C. under vacuum overnight to afford the desired product as a white solid (2.20 g, 85%).

$^1$H NMR (500 MHz, $D_2O$) δ 7.51 (br d, J=7.9 Hz, 2H), 7.44 (d, J=7.9 Hz, 1.5H), 7.37 (br d, J=7.9 Hz, 0.5H), 7.19 (d, J=3.1 Hz, 1H), 6.41 (d, J=3.0 Hz, 1H), 3.81 (t, J=5.7 Hz, 1.5H), 3.69-3.65 (m, 0.5H), 3.31 (t, J=5.7 Hz, 1.5H), 3.15 (t, J=6.3 Hz, 0.5H), 3.05 (s, 0.8H), 3.01 (s, 2.2H), 2.72 (s, 2.2H), 2.53 (s, 0.8H). Multiple rotamers are observed. LC-MS (Method B): $R_T$=4.93 min, m/z=379.7 $[M-H]^-$.

Example 2—Alternative Conditions for Step 3 of Example 1: The Synthesis of Benzyl 3-[4-[2-[Benzyloxycarbonyl(methyl)amino]ethyl-methyl-carbamoyl]phenyl]-1-(benzyloxycarbonylsulfamoyl)pyrrole-2-carboxylate

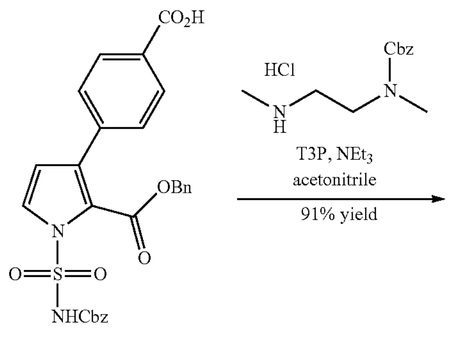

-continued

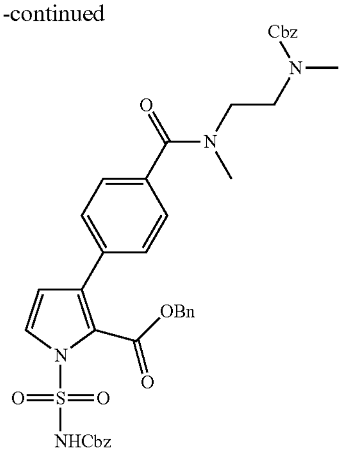

To a suspension of benzyl N-methyl-N-[2-(methylamino)ethyl]carbamate hydrochloride (25.4 g, 98.2 mmol) and 4-[2-benzyloxycarbonyl-1-(benzyloxycarbonylsulfamoyl)pyrrol-3-yl]benzoic acid (50.0 g, 93.5 mmol) in acetonitrile (125 mL) was added triethylamine (78.2 mL, 561 mmol) before stirring for 20 minutes at 20° C. Propanephosphonic acid anhydride (50% in ethyl acetate, 82.7 mL, 140 mmol) was added over a period of 1 hour, ensuring that the temperature was maintained below 25° C., before stirring at room temperature for a further 1 hour. The reaction mixture was diluted with ethyl acetate (500 mL) and 5% aqueous citric acid solution (500 mL) then stirred for 15 minutes. The layers were separated and the organic phase sequentially washed with 5% aqueous citric acid solution (500 mL) and 1M aqueous sodium bicarbonate solution (500 mL). The organic phase was concentrated to a final volume of 100 mL, forming a mobile slurry which was diluted with ethyl acetate (150 mL) and stirred overnight at 20° C. n-Heptane (100 mL) was added to the slurry over 4 hours and the mixture stirred overnight.

The product was isolated by filtration and washed with 1:3 ethyl acetate:n-heptane (100 mL), n-heptane (100 mL) and dried under vacuum at 40° C. overnight to give the desired product as a white solid (63.0 g, 91%).

Analytical data was consistent with that reported in step 3 of Example 1.

Example 3—Alternative Conditions for Step 4 of Example 1: The Synthesis of 3-[4-[Methyl-[2-(methylamino)ethyl]carbamoyl]phenyl]-1-sulfamoyl-pyrrole-2-carboxylic Acid

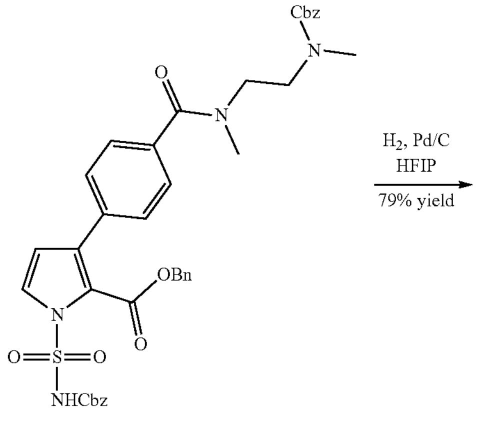

-continued

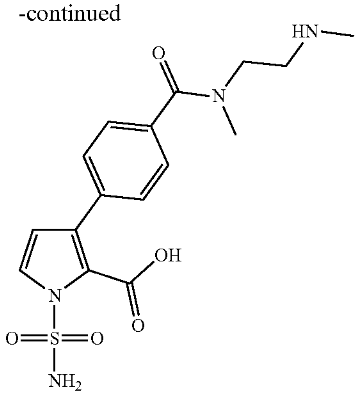

A mixture of benzyl 3-[4-[2-[benzyloxycarbonyl(methyl)amino]ethyl-methyl-carbamoyl]phenyl]-1-(benzyloxycarbonylsulfamoyl)pyrrole-2-carboxylate (100 g, 135 mmol) and 10% palladium on activated carbon (Type 58, standard, reduced, nominally 50% water wet, 4.50 g, 2.13 mmol) in HFIP (500 mL) was purged three times with vacuum/nitrogen then three times with hydrogen before pressurizing to ~850 mbar hydrogen. The reaction mixture was maintained at this pressure at 20° C. for 24 hours then purged with nitrogen and filtered through a pad of Solka-floc (60 g), washing with HFIP (150 mL). The combined filtrates were stirred with SEM26 (60 g) at 20° C. for 68 hours, then filtered through filter paper washing with HFIP (150 mL). The combined filtrates were concentrated under reduced pressure to a final volume of 200 mL, followed by the addition of water (100 mL) and methanol (100 mL) and finally product seed crystals (200 mg). The mixture was stirred for 30 min at 20° C., methanol (300 mL) was added over 2 hours and the resulting slurry was stirred overnight. The slurry was filtered and the cake washed with 80:20 methanol:water (2×300 mL) and dried overnight at 30° C. under vacuum to give crude product as a white solid (44.5 g, 87% crude yield).

Recrystallisation step: A suspension of the crude product (40.6 g, 107 mmol) in DMSO (160 mL) was stirred at 20° C. until a solution was formed. Water (200 mL) was added over 1 hour maintaining the temperature below 25° C. and the resulting slurry stirred for 1 hour. Methanol (240 mL) was charged over 1 hour and the mixture stirred overnight. The resulting slurry was filtered and the cake washed with 80:20 methanol:water (2×120 mL) and dried on the filter under vacuum. The damp cake was then slurried in a mixture of methanol (400 mL) and water (40 mL) for 20 hours at 20° C., isolated by filtration, washed with 80:20 methanol:water (240 mL) and dried overnight at 30° C. under vacuum to give the desired product as a white solid (37.1 g, 91% recrystallisation yield, overall 79% yield).

Analytical data was consistent with that reported in step 4 of Example 1.

Example 4—Alternative Conditions for Step 4 of Example 1: The Synthesis of 3-[4-[Methyl-[2-(methylamino)ethyl]carbamoyl]phenyl]-1-sulfamoyl-pyrrole-2-carboxyl is Acid

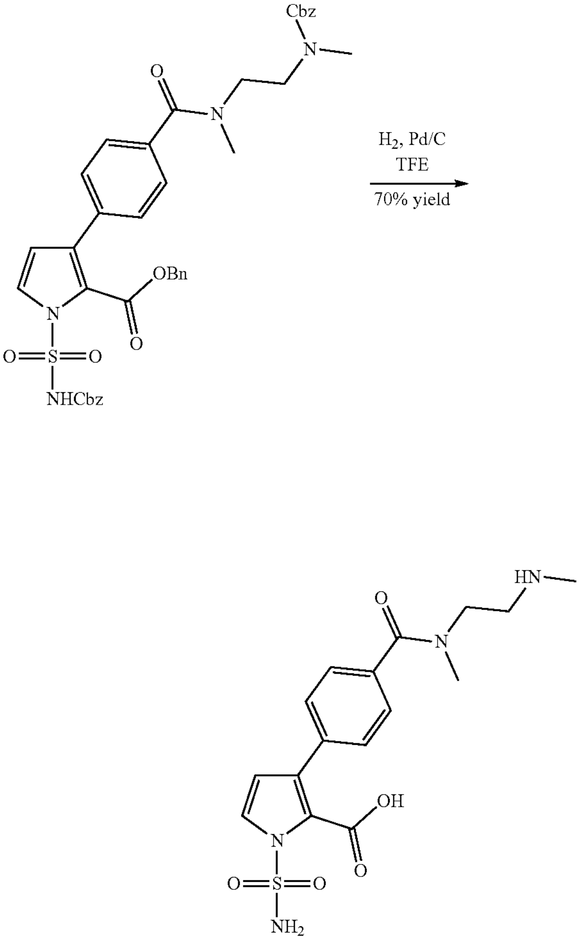

A mixture of benzyl 3-[4-[2-[benzyloxycarbonyl(methyl)amino]ethyl-methyl-carbamoyl]phenyl]-1-(benzyloxycarbonylsulfamoyl)pyrrole-2-carboxylate (20 g, 27 mmol) and 10% palladium on activated carbon (nominally 50% water wet, 2.0 g, 0.94 mmol) in TFE (1000 mL) was purged two times with vacuum/nitrogen then three times with hydrogen before pressurizing to 2-4 atm hydrogen. The reaction mixture was maintained at this pressure at room temperature for 16 hours then purged with nitrogen and filtered, washing with TFE (20 mL). The combined filtrates were concentrated under reduced pressure to a final volume of 160 mL, stirred for 6 hours before isolation of the precipitated solid by filtration. The solid was resuspended in methanol (400 mL), stirred for 2 hours, isolated by filtration and washed with methanol (60 mL). The filtered solid was resuspended in a mixture of methanol (200 mL) and water (200 mL) and stirred for 2 hours. The solid was isolated by filtration, washed with methanol (60 mL) and dried under vacuum at 40° C. for 8 hours to give the desired product as a white solid (7.2 g, 70%).

Analytical data was consistent with that reported in step 4 of Example 1.

Example 5—Alternative Synthetic Route to 4-[2-Benzyloxycarbonyl-1-(benzyloxycarbonylsulfamoyl) pyrrol-3-yl]benzoic Acid (Via Sodium Salt)

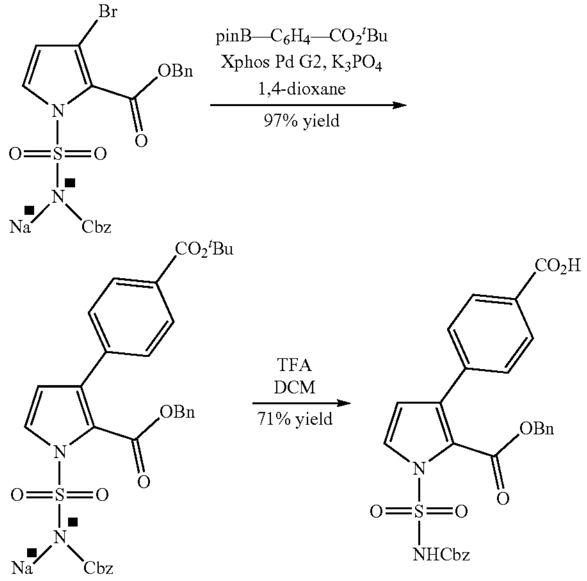

Step 1: Sodium [(benzyloxy)carbonyl]{2 [benzyloxy)carbonyl]-3-{4-[(tert-butoxy)carbonyl]phenyl}-1H-pyrrol-1-yl}sulfonyl)azanide A stirred suspension of sodium benzyloxycarbonyl-(2-benzyloxycarbonyl-3-bromo-pyrrol-1-yl)sulfonyl-azanide (35.0 g, 67.9 mmol), tert-butyl 4-(4,4,5,5-tetramethyl-1,3,2-dioxaborolan-2-yl)benzoate (22.7 g, 74.7 mmol) and XPhos Pd G2 (2.67 g, 3.40 mmol) in 1,4-dioxane (350 mL) was degassed and purged with nitrogen followed by the addition of 3M aqueous $K_3PO_4$ solution (67.9 mL, 204 mmol). After heating at 45° C. for 2 hours, the reaction mixture was allowed to cool, the phases separated and the organic phase concentrated to dryness. The residue was redissolved in ethyl acetate (300 mL), washed with water (2×300 mL) and saturated sodium bicarbonate solution (2×300 mL), dried over $MgSO_4$, filtered and concentrated to −60 mL under reduced pressure. This was diluted with diethyl ether (150 mL) and the resulting solution added dropwise to petroleum ether with vigorous stirring. The precipitated solid was isolated by filtration and sucked dry to give the desired product as an off-white solid (40.4 g, 97%).

$^1$H NMR (500 MHz, $CDCl_3$) δ 7.61 (br d, J=7.6 Hz, 2H), 7.56 (br s, 1H), 7.11-6.86 (m, 11H), 6.58 (br d, J=6.7 Hz, 2H), 5.87 (br s, 1H), 4.86 (br s, 2H), 4.78 (s, 2H), 1.61 (s, 9H). LC-MS (Method A): $R_T$=3.93 min, m/z=589.6 $[M-H]^-$.

Step 2: 4-[2-Benzyloxycarbonyl-1-(benzyloxycarbonylsulfamoyl)pyrrol-3-yl]benzoic Acid To a stirred solution of sodium [(benzyloxy)carbonyl]({2-[(benzyloxy)carbonyl]-3-{4-[(tert-butoxy)carbonyl]phenyl}-1H-pyrrol-1-yl}sulfonyl)azanide (40.5 g, 65.8 mmol) in DCM (300 mL) was added TFA (73 mL, 0.99 mol). The reaction mixture was stirred at room temperature for 1 hour, then concentrated to dryness. The residue was triturated with isopropanol, filtered and sucked dry to give the desired product as an off-white solid (25.0 g, 71%). This was used in the subsequent steps without any further removal of residual salts.

$^1$H NMR (500 MHz, DMSO-$d_6$) δ 7.85 (br d, J=7.9 Hz, 2H), 7.49 (br s, 1H), 7.44-7.23 (m, 10H), 7.19 (br d, J=6.4 Hz, 2H), 6.51 (br s, 1H), 5.22 (s, 2H), 5.12 (s, 2H). LC-MS (Method A): $R_T$=3.20 min, m/z=533.5 $[M-H]^-$.

Compound IVa is synthesised from 4-[2-Benzyloxycarbonyl-1-(benzyloxycarbonylsulfamoyl)pyrrol-3-yl]benzoic acid according to the methods of steps 3 and 4 of Example 1.

Example 6—Alternative Synthetic Route to 4-[2-Benzyloxycarbonyl-1-(benzyloxycarbonylsulfamoyl) pyrrol-3-yl]benzoic acid (via free sulfonamide)

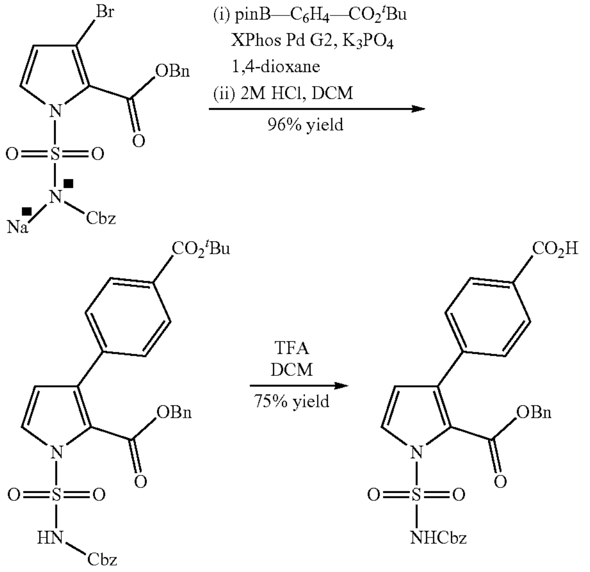

Step 1: Benzyl 1-(benzyloxycarbonylsulfamoyl)-3-(4-tert-butoxycarbonylphenyl)pyrrole-2-carboxylate Sodium benzyloxycarbonyl-(2-benzyloxycarbonyl-3-bromo-pyrrol-1-yl)sulfonyl-azanide (51.9 g, 101 mmol) was converted to sodium [(benzyloxy)carbonyl]({2-[(benzyloxy)carbonyl]-3-{4-[(tert-butoxy)carbonyl]phenyl}-1H-pyrrol-1-yl}sulfonyl)azanide in a similar manner to that described above. This was redissolved in DCM (500 mL), washed with 2M aqueous HCl (500 mL), dried over $Na_2SO_4$, filtered and concentrated to dryness to give the desired product as an off-white solid (58.0 g, 96%).

LC-MS (Method A): $R_T$=4.12 min, m/z=589.6 $[M-H]^-$.

Step 2: 4-[2-Benzyloxycarbonyl-1-(benzyloxycarbonylsulfamoyl)pyrrol-3-yl]benzoic Acid To a stirred solution of benzyl 1-(benzyloxycarbonylsulfamoyl)-3-(4-tert-butoxycarbonylphenyl)pyrrole-2-carboxylate (58.0 g, 98.2 mmol) in DCM (300 mL) was added TFA (109 mL, 1.47 mol). The reaction mixture was stirred at room temperature for 2 hours, then concentrated to dryness. The residue was triturated with isopropanol, filtered and sucked dry to give the desired product as an off-white solid (39.2 g, 75%).

$^1$H NMR (500 MHz, $CDCl_3$) δ 8.68 (br s, 1H), 7.94 (br d, J=7.6 Hz, 2H), 7.65 (br s, 1H), 7.40-7.21 (m, 10H), 7.00 (br d, J=7.0 Hz, 2H), 6.29 (br s, 1H), 5.19 (s, 2H), 5.11 (s, 2H). LC-MS (Method A): $R_T$=3.17 min, m/z=533.5 $[M-H]^-$.

Compound IVa is synthesised from 4-[2-Benzyloxycarbonyl-1-(benzyloxycarbonylsulfamoyl)pyrrol-3-yl]benzoic acid according to the methods of steps 3 and 4 of Example 1.

Example 7—Alternative Synthetic Route to benzyl 3-[4-[2-[benzyloxycarbonyl(methyl)amino]ethyl-methyl-carbamoyl]phenyl]-1-(benzyloxycarbonylsulfamoyl)pyrrole-2-carboxylate

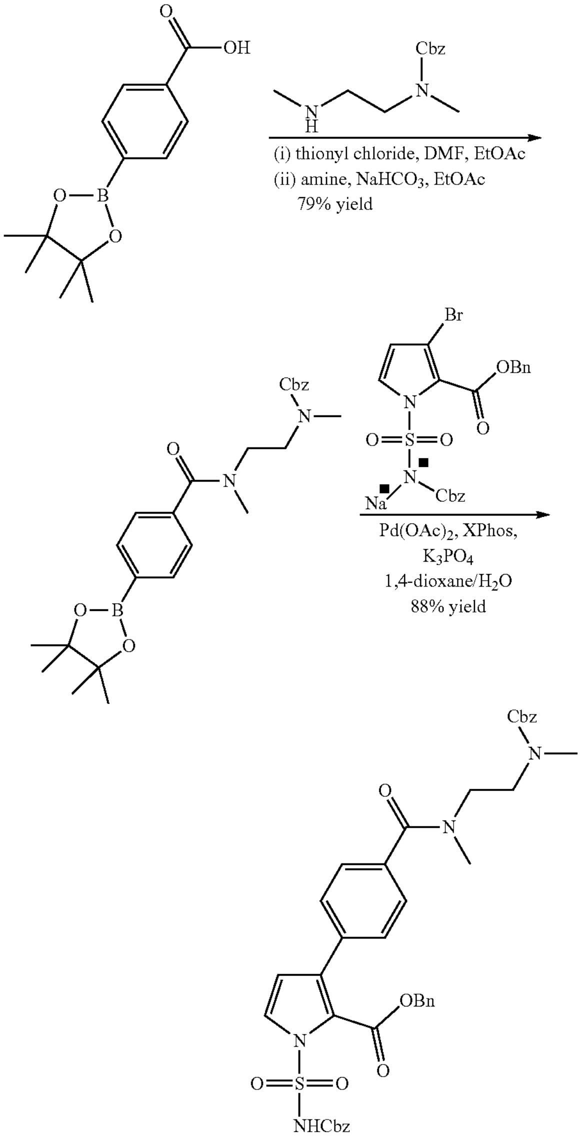

Step 1: Benzyl N-methyl-N-[2-[methyl-[4-(4,4,5,5-tetramethyl-1,3,2-dioxaborolan-2-yl)benzoyl]amino]ethyl]carbamate To a suspension of 4-(4,4,5,5-tetramethyl-1,3,2-dioxaborolan-2-yl)benzoic acid (1.0 g, 4.03 mmol) in ethyl acetate (10 mL) was added DMF (6 μL, 81 μmol). After cooling to 0° C., thionyl chloride (0.32 mL, 4.43 mmol) was added dropwise before allowing the reaction mixture to warm to room temperature and stirring overnight. The resulting solution was concentrated under reduced pressure to approximately half the volume followed by the addition of solid sodium bicarbonate (745 mg, 8.87 mmol) then the dropwise addition of a solution of benzyl N-methyl-N-[2-(methylamino)ethyl]carbamate (986 mg, 4.43 mmol) in ethyl acetate (5 mL). After stirring at room temperature for 1 hour, the reaction mixture was filtered. The filtrates were concentrated to −5 mL followed by the addition of petroleum ether (40 mL) and stirring for 10 minutes. The precipitated solid was isolated by filtration and sucked dry to give the desired product as a white solid (1.44 g, 79%).

$^1$H NMR (500 MHz, $CDCl_3$) δ 7.85-7.77 (m, 2H), 7.39-7.20 (m, 7H), 5.18-4.93 (m, 2H), 3.77-2.63 (m, 10H), 1.35 (s, 12H). LC-MS (Method A): $R_T$=3.65 min, m/z=453.6 $[M+H]^+$.

Step 2: Benzyl 3-[4-[2-[Benzyloxycarbonyl(methyl)amino]ethyl-methyl-carbamoyl]phenyl]-1-(benzyloxycarbonylsulfamoyl)pyrrole-2-carboxylate XPhos (278 mg, 0.58 mmol) and palladium(II) acetate (44 mg, 0.19 mmol) were pre-stirred in 1,4-dioxane (5 mL) for 5 minutes before the addition of sodium benzyloxycarbonyl-(2-benzyloxycarbonyl-3-bromo-pyrrol-1-yl)sulfonyl-azanide (2.00 g, 3.88 mmol) and benzyl N-methyl-N-[2-[methyl-[4-(4,4,5,5-tetramethyl-1,3,2-dioxaborolan-2-yl)benzoyl]amino]ethyl]carbamate (2.28 g, 5.05 mmol) with 1,4-dioxane (10 mL). The mixture was degassed and placed under a nitrogen atmosphere before addition of 3M aqueous $K_3PO_4$ solution (3.88 mL, 11.6 mmol) and heating to 60° C. for 2.5 hours. The reaction mixture was diluted with ethyl acetate (~100 mL) and washed with water (2×~60 mL) and brine (~60 mL). The organic phase was dried over $Na_2SO_4$, filtered and concentrated to dryness, then the residue re-concentrated from IPA, triturated with diethyl ether and isolated by filtration. The isolated solid was redissolved in DCM with the aid of methanol and acidified by washing with 1M aqueous HCl solution. The organic phase was dried over $Na_2SO_4$, filtered, concentrated to dryness, then re-concentrated from a mixture of DCM and petroleum ether to give the desired product as an off-white solid (2.55 g, 88%).

$^1$H NMR (500 MHz, $CDCl_3$) δ 8.64 (br s, 1H), 7.55 (d, J=3.1 Hz, 1H), 7.39-7.20 (m, 17H), 7.10-7.01 (br m, 2H), 6.25 (d, J=2.4 Hz, 1H), 5.20-4.95 (m, 6H), 3.76 (br t, J=5.5 Hz, 1H), 3.70-3.57 (br m, 2H), 3.45-3.28 (br m, 1H), 3.20-2.76 (m, 5H), 2.72-2.61 (br m, 1H). LC-MS (Method A): $R_T$=3.31 min, m/z=739.5 $[M+H]^+$.

Compound IVa is synthesised from benzyl 3-[4-[2-[Benzyloxycarbonyl(methyl)amino]ethyl-methyl-carbamoyl]phenyl]-1-(benzyloxycarbonylsulfamoyl)pyrrole-2-carboxylate according to the method of step 4 of Example 1.

Example 8—Alternative Synthetic Route to benzyl 3-[4-[2-[benzyloxycarbonyl(methyl)amino]ethyl-methyl-carbamoyl]phenyl]-1-(benzyloxycarbonylsulfamoyl)pyrrole-2-carboxylate (Via Coupling with Chloride)

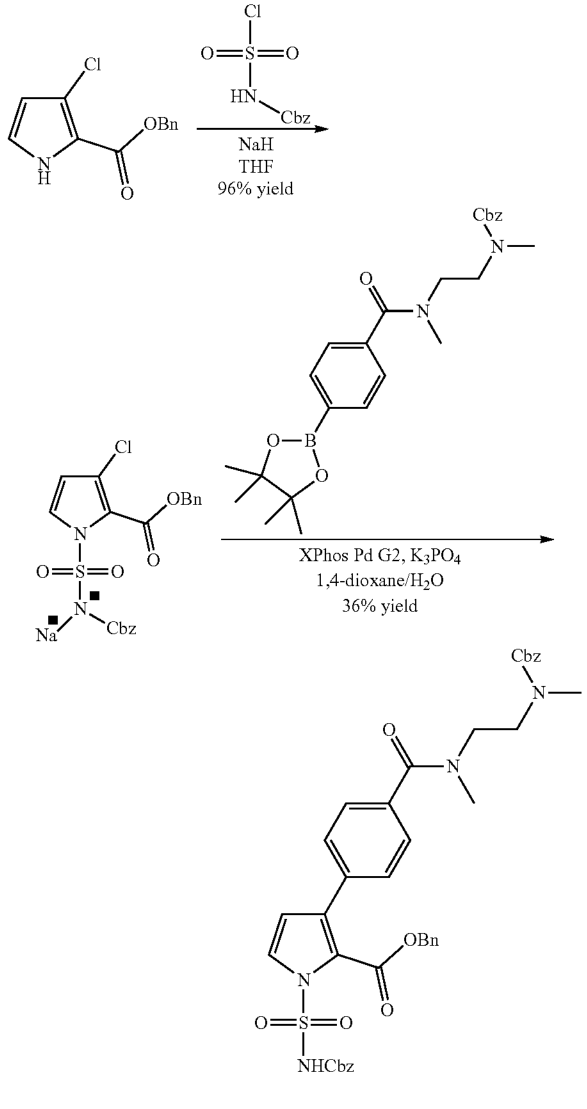

Step 1: Sodium benzyloxycarbonyl-(2-benzyloxy-carbonyl-3-chloro-pyrrol-1-yl)sulfonyl-azanide A suspension of sodium hydride (60% in mineral oil, 25.2 g, 630 mmol) in anhydrous THF (200 mL) was cooled to −10° C. under a nitrogen atmosphere followed by the dropwise addition of a solution of benzyl 3-chloro-1H-pyrrole-2-carboxylate (49.5 g, 210 mmol) in anhydrous THF (200 mL) over a period of 60 minutes ensuring that the temperature was maintained below −5° C. The reaction mixture was allowed to warm to room temperature and stirred for 1 hour before recooling to −10° C. To the reaction mixture was added benzyl N-chlorosulfonylcarbamate (57.7 g, 231 mmol) portionwise over a period of 45 minutes ensuring that the temperature was maintained below −5° C. The reaction mixture was allowed to warm to room temperature and stirred for 2 hours, then recooled to −10° C. and quenched by the dropwise addition of 50:50 water:brine (250 mL). The mixture was extracted into ethyl acetate (3×100 mL) and the combined organic phases washed with brine (200 mL), dried over $MgSO_4$, the solution decanted and concentrated to dryness. The residue was triturated in diethyl ether (200 mL), filtered and sucked dry to give the desired product as a white solid (94.5 g, 96%).

$^1H$ NMR (500 MHz, DMSO-$d_6$) δ 7.54-7.50 (m, 2H), 7.36-7.25 (m, 9H), 6.13 (d, J=3.1 Hz, 1H), 5.23 (s, 2H), 4.85 (s, 2H). LC-MS (Method A): $R_T$=3.48 min, m/z=447.2/449.2 $[M-H]^-$.

Step 2: Benzyl 3-[4-[2-[benzyloxycarbonyl(methyl)amino]ethyl-methyl-carbamoyl]phenyl]-1-(benzyloxycarbonylsulfamoyl)pyrrole-2-carboxylate A mixture of sodium benzyloxycarbonyl-(2-benzyloxy-carbonyl-3-chloro-pyrrol-1-yl)sulfonyl-azanide (500 mg, 1.06 mmol) and benzyl N-methyl-N-[2-[methyl-[4-(4,4,5,5-tetramethyl-1,3,2-dioxaborolan-2-yl)benzoyl]amino]ethyl]carbamate (606 mg, 1.34 mmol) in 1,4-dioxane (4 mL) was degassed by bubbling nitrogen for 5 minutes, followed by the addition of XPhos Pd G2 (88 mg, 0.11 mmol) and a solution of $K_3PO_4$ (711 mg, 3.35 mmol) in water (1 mL). The reaction mixture was then heated to 50° C. under a nitrogen atmosphere for 2 hours. After this period, the reaction mixture was allowed to cool to room temperature, diluted with 50:50 water:brine (3 mL) and extracted into ethyl acetate (3×3 mL). The combined organic phases were washed with 2M aqueous HCl solution (5 mL) and brine (5 mL), dried over $MgSO_4$, filtered and concentrated to dryness under reduced pressure. The residue was purified by column chromatography (silica, petroleum ether:ethyl acetate, gradient elution from 90:10 to 0:100) to give the desired product as a pale yellow solid (280 mg, 36% yield).

$^1H$ NMR (500 MHz, DMSO-$d_6$) δ 7.45-7.17 (m, 20H), 6.46-6.32 (m, 1H), 5.19 (br s, 2H), 5.13-4.99 (m, 4H), 3.71-2.72 (m, 10H). LC-MS (Method A): $R_T$=3.73 min, m/z=740.0 $[M+H]^+$.

Compound IVa is synthesised from benzyl 3-[4-[2-[Benzyloxycarbonyl(methyl)amino]ethyl-methyl-carbamoyl]phenyl]-1-(benzyloxycarbonylsulfamoyl)pyrrole-2-carboxylate according to the method of step 4 of Example 1.

Example 9—Alternative Synthetic Route to benzyl 3-[4-[2-[benzyloxycarbonyl(methyl)amino]ethyl-methyl-carbamoyl]phenyl]-1-(benzyloxycarbonylsulfamoyl)pyrrole-2-carboxylate

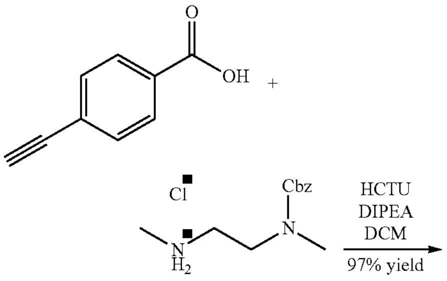

-continued

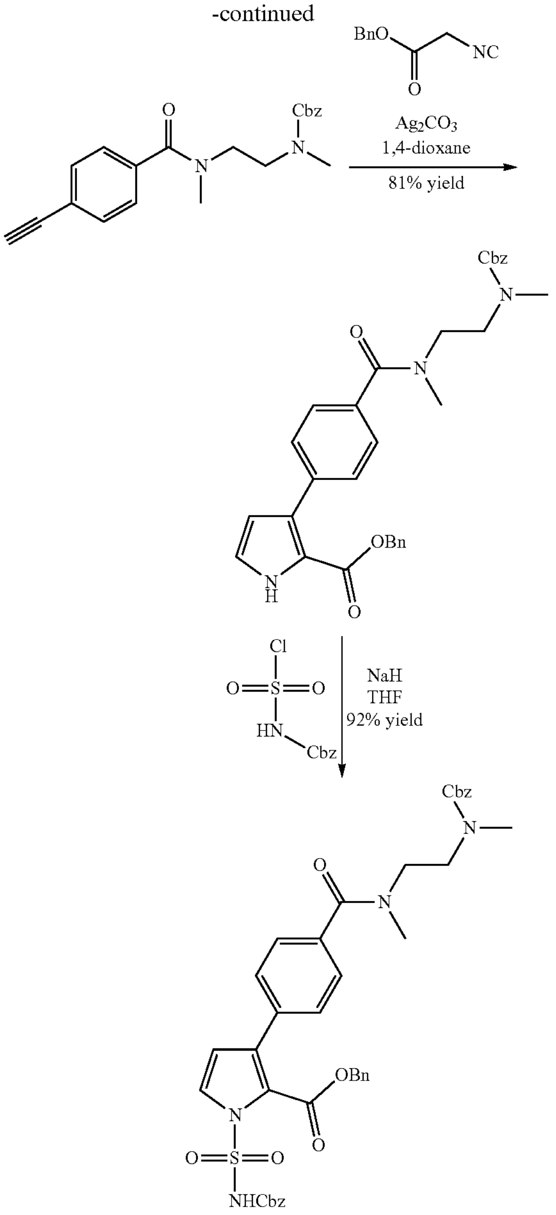

Step 1: Benzyl N-{2-[1-(4-ethynylphenyl)-N-methylformamido]ethyl}-N-methylcarbamate To a mixture of 4-ethynylbenzoic acid (6.86 g, 46.9 mmol) and benzyl N-methyl-N-[2-(methylamino)ethyl]carbamate hydrochloride (13.4 g, 51.6 mmol) in DCM (150 mL) was added HBTU (23.1 g, 61.0 mmol) followed by DIPEA (36.1 mL, 211 mmol) before stirring at 20° C. for 3 days. The reaction mixture was concentrated to dryness and redissolved in ethyl acetate (400 mL), washed with 2M aqueous HCl (2×200 mL), water (200 mL), saturated aqueous sodium bicarbonate solution (2×200 mL), water (200 mL) and brine (100 mL). The organic phase was dried over $MgSO_4$, filtered, concentrated to dryness and purified by column chromatography (silica, petroleum ether:ethyl acetate, gradient elution from 100:0 to 0:100) to give the desired product as a straw-coloured gum (16.0 g, 97%).

$^1$H NMR (500 MHz, $CDCl_3$) δ 7.47 (br d, J=7.8 Hz, 2H), 7.40-7.25 (m, 7H), 5.20-4.90 (m, 2H), 3.74 (t, J=5.2 Hz,

1H), 3.68-3.27 (br m, 3H), 3.17-2.79 (m, 6H), 2.76-2.65 (br m, 1H). LC-MS (Method C): $R_T$=1.76 min, m/z=351.2 $[M+H]^+$.

Step 2: Benzyl 3-{4-[(2-{[benzyloxy)carbonyl]methyl)amino}ethyl)(methyl)carbamoyl]phenyl}-1H-pyrrole-2-carboxylate A mixture of benzyl N-{2-[1-(4-ethynyl phenyl)-N-methylformamido]ethyl}-N-methylcarbamate (3.50 g, 9.99 mmol) and silver carbonate (551 mg, 2.00 mmol) in anhydrous 1,4-dioxane (10 mL) was heated to 100° C. under an argon atmosphere. To the heated suspension was added dropwise (~80 minutes via syringe pump) a solution of benzyl 2-isocyanoacetate (2.10 g, 12.0 mmol) in anhydrous 1,4-dioxane (10 mL) before heating at 100° C. for a further 2 hours. After cooling to room temperature the reaction mixture was diluted with diethyl ether (200 mL) and stirred for 10 minutes, then filtered through Celite®. The filtrate was concentrated to dryness to give the desired product as a yellow gum (4.26 g, 81%).

$^1$H NMR (500 MHz, $CDCl_3$) δ 9.28 (br s, 1H), 7.54 (br d, J=7.8 Hz, 2H), 7.40-7.25 (m, 12H), 6.95 (t, J=2.7 Hz, 1H), 6.34 (br s, 1H), 5.24 (s, 2H), 5.20-4.92 (m, 2H), 3.76 (br s, 1H), 3.69-3.26 (br m, 3H), 3.20-2.82 (br m, 5H), 2.75-2.55 (br m, 1H). LC-MS (Method C): $R_T$=1.98 min, m/z=526.3 $[M+H]^+$.

Step 3: Benzyl 3-[4-[2-[benzyloxycarbonyl(methyl)amino]ethyl-methyl-carbamoyl]phenyl]-1-(benzyloxycarbonylsulfamoyl)pyrrole-2-carboxylate A suspension of sodium hydride (60% in mineral oil, 228 mg, 5.71 mmol) in anhydrous THF (5 mL) was cooled to −10° C. under an argon atmosphere followed by the dropwise addition of a solution of benzyl 3-{4-[(2-{[(benzyloxy)carbonyl]methyl)amino}ethyl)(methyl)carbamoyl]phenyl}-1H-pyrrole-2-carboxylate (1.00 g, 1.90 mmol) in anhydrous THF (5 mL) over a period of 30 minutes. The reaction mixture was allowed to warm to room temperature and stirred for a further 60 minutes before re-cooling to −10° C. To the reaction mixture was added benzyl N-chlorosulfonylcarbamate (523 mg, 2.09 mmol) portionwise over a period of 25 minutes, then the mixture allowed to warm to room temperature and stirred for a further 2 hours. The reaction mixture was recooled to −10° C., carefully quenched with 1:1 brine:water solution (20 mL), acidified with 2M aqueous HCl (50 mL) and extracted into ethyl acetate (3×50 mL). The combined organic phases were washed with brine (50 mL), dried over $MgSO_4$, filtered and concentrated to dryness to give crude product as a colourless gum (1.29 g, 92%).

$^1$H NMR (500 MHz, $CDCl_3$) δ 8.67 (br s, 1H), 7.55 (d, J=3.2 Hz, 1H), 7.40-7.20 (m, 17H), 7.05 (br s, 2H), 6.15 (br d, J=2.3 Hz, 1H), 5.20-5.00 (m, 6H), 3.79-3.72 (br m, 1H), 3.70-3.56 (br m, 2H), 3.45-3.29 (br m, 1H), 3.18-2.77 (br m, 5H), 2.71-2.62 (br m, 1H). LC-MS (Method C): $R_T$=2.17 min, m/z=739.3 $[M+H]^+$.

Compound IVa is synthesised from benzyl 3-[4-[2-[benzyloxycarbonyl(methyl)amino]ethyl-methyl-carbamoyl]phenyl]-1-(benzyloxycarbonylsulfamoyl)pyrrole-2-carboxylate according to the method of step 4 of Example 1.

The invention claimed is:

1. A method of forming a compound of formula (IV) or a pharmaceutically acceptable salt thereof, the method comprising (a) reacting the compound of formula (I) with the compound of formula (II) in the presence of Pd/C to form the compound of formula (III):

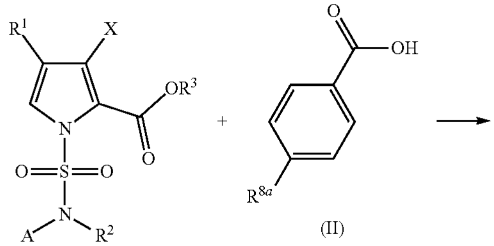

(I) (II)

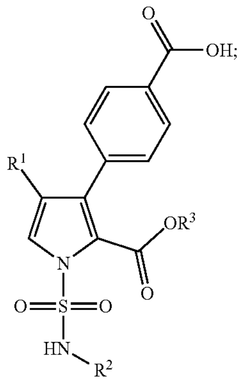

(III)

and (b) forming a compound of formula (IV) or a pharmaceutically acceptable salt thereof from the compound of formula (III):

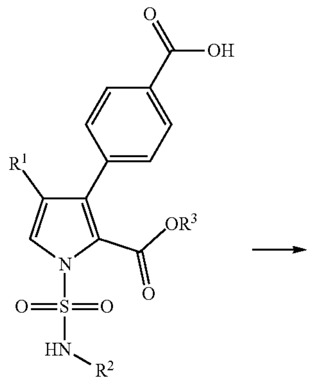

(III)

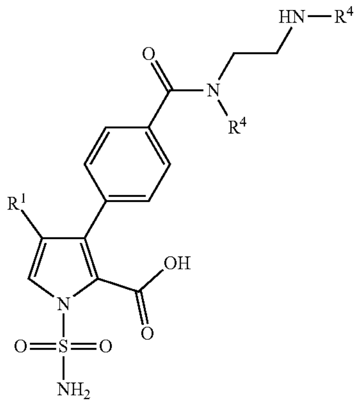

(IV)

wherein

X is independently selected from Cl, Br, I, $N_2^+$ or $OSO_2CF_3$;

$R^1$ is independently selected from H or $C_{1-4}$ alkyl;

$R^2$ is a protecting group;

$R^3$ is independently selected from —$CH_2$-aryl or tert-butyl;

each $R^4$ is independently at each occurrence a $C_{1-4}$ alkyl;

$R^{8a}$ is $BF_3K$ or $B(OR^{9a})_2$; wherein either $R^{9a}$ is at each occurrence H or $C_{1-4}$ alkyl; or the two $R^{9a}$ substituents together form $(CR^aR^b)_n$; or the two $R^{9a}$ substituents together form —C(O)—$(CR^aR^b)$—N$(R^c)$—$(CR^aR^b)$—C(O)—;

$R^a$, $R^b$ and $R^c$ are independently selected at each occurrence from H and $C_{1-4}$ alkyl;

n is 2 or 3;

and

A is independently selected from H or a cation.

2. The method of claim 1, wherein step (b) comprises the steps of (i) reacting the compound of formula (III) with a compound of formula (V) to form the compound of formula (VI):

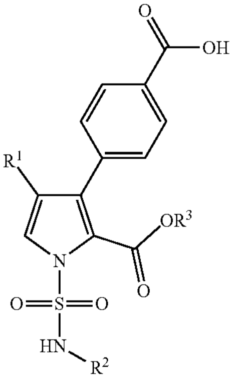

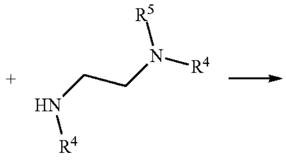

(III) (V)

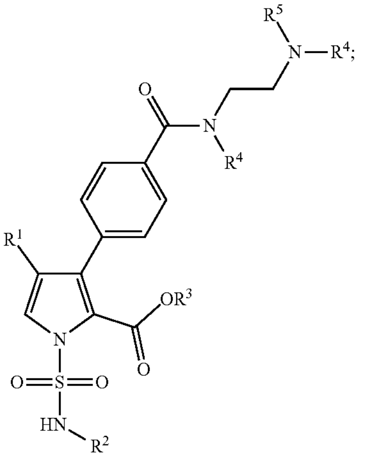

(VI)

and (ii) cleaving the $R^2$, $R^3$ and $R^5$ substituents from the compound of formula (VI) to form the compound of formula (IV) or a pharmaceutically acceptable salt thereof:

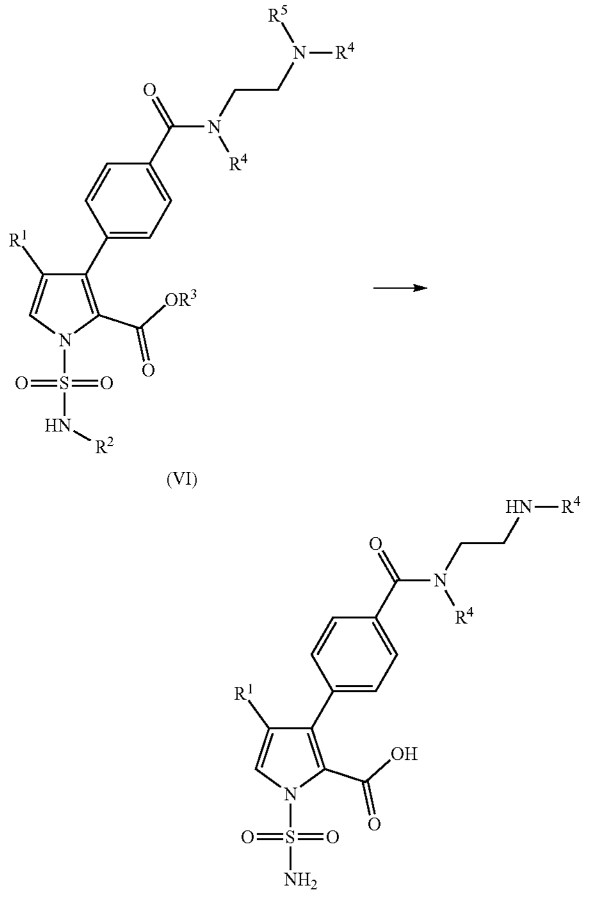
(VI)
(IV)
wherein
$R^5$ is a protecting group.
3. The method of claim 1, wherein the compound of formula (I) is formed by reacting a compound of formula (VII) with a compound of formula (VIII) to form the compound of formula (I):
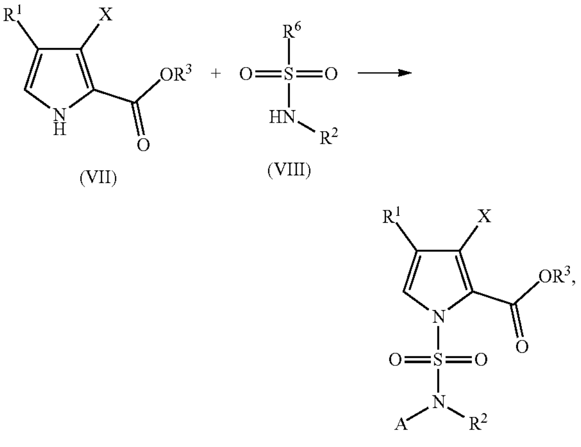
(VII) (VIII)
(I)
wherein $R^6$ is independently selected from F, Cl, Br, I, or
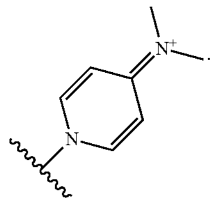 [SMILES: *n1ccc(=[N+](C)C)cc1]
* * * * *